United States Patent
Caseres et al.

(10) Patent No.: US 7,314,636 B2
(45) Date of Patent: Jan. 1, 2008

(54) BIODEGRADABLE INJECTABLE IMPLANTS CONTAINING GLYCOLIC ACID

(75) Inventors: Crisoforo Peralta Caseres, Mexico City (MX); Daniel Leon de Lagarde, Mexico City (MX)

(73) Assignee: Medgraft Microtech, Inc., Valencia (ES)

(*) Notice: Subject to any disclaimer, the term of this patent is extended or adjusted under 35 U.S.C. 154(b) by 621 days.

(21) Appl. No.: 10/186,183

(22) Filed: Jun. 28, 2002

(65) Prior Publication Data

US 2003/0093157 A1    May 15, 2003

Related U.S. Application Data

(63) Continuation-in-part of application No. 10/002,283, filed on Dec. 5, 2001, now abandoned.

(30) Foreign Application Priority Data

Jun. 29, 2001 (MX) .................... PA/A/2001/006732

(51) Int. Cl.
  *A61F 2/00* (2006.01)
(52) U.S. Cl. .................... 424/426; 514/772.6
(58) Field of Classification Search ............... 424/426; 514/772.6
  See application file for complete search history.

(56) References Cited

U.S. PATENT DOCUMENTS

| 4,874,612 A | 10/1989 | Deasy ..................... 424/425 |
| 5,227,412 A | 7/1993 | Hyon et al. ................. 523/105 |
| 5,571,182 A | 11/1996 | Ersek et al. ................. 623/11 |
| 5,645,856 A * | 7/1997 | Lacy et al. ................. 424/455 |
| 5,733,572 A * | 3/1998 | Unger et al. ................ 424/450 |
| 5,766,631 A | 6/1998 | Arnold ...................... 424/486 |
| 5,788,978 A * | 8/1998 | Passeron et al. ............. 424/426 |
| 5,922,025 A | 7/1999 | Hubbard ..................... 623/11 |
| 5,942,241 A * | 8/1999 | Chasin et al. ............... 424/426 |
| 6,281,015 B1 * | 8/2001 | Mooney et al. .............. 435/395 |
| 6,291,013 B1 * | 9/2001 | Gibson et al. ............. 427/213.3 |
| 6,303,137 B1 | 10/2001 | Dittgen et al. ............. 424/426 |
| 6,451,335 B1 * | 9/2002 | Goldenheim et al. ........ 424/426 |
| 2002/0131951 A1 * | 9/2002 | Langer et al. ........... 424/78.37 |

(Continued)

FOREIGN PATENT DOCUMENTS

DE    3916020 A1 *  11/1990

(Continued)

OTHER PUBLICATIONS

U.S. Appl. No. 60/239,330, to Langer et al filed Oct. 10, 2000.*

(Continued)

*Primary Examiner*—Paul B. Prebilic
(74) *Attorney, Agent, or Firm*—Vinson & Elkins LLP

(57) ABSTRACT

This invention is directed to the field of medical implants, and more specifically to biodegradable injectable implants and their methods of manufacture and use. The injectable implants disclosed herein comprise glycolic acid and biocompatible/bio-absorbable polymeric particles containing a polymer of lactic acid. The particles are small enough to be injected through a needle but large enough to avoid engulfment by macrophages. The injectables of this invention may be in a pre-activated solid form or an activated form (e.g., injectable suspension or emulsion).

69 Claims, 5 Drawing Sheets

U.S. PATENT DOCUMENTS

2006/0159721 A1* 7/2006 Siegel et al. ............ 424/426

FOREIGN PATENT DOCUMENTS

| EP | 0 281 779 A1 | 2/1988 |
| EP | 0 353 172 A2 | 7/1989 |
| EP | 0 608 921 A2 | 5/1990 |
| EP | 0 608 921 A3 | 5/1990 |
| EP | 0 481 732 A1 | 10/1991 |
| EP | 0 508 730 A1 | 4/1992 |
| EP | 1 080 698 A1 | 2/1993 |
| EP | 1 080 699 A1 | 2/1993 |
| EP | 1 080 737 A1 | 2/1993 |
| EP | 0 567 391 A1 | 4/1993 |
| EP | 0 669 128 A1 | 11/1993 |
| EP | 1 036 865 A1 | 3/2000 |
| WO | WO 89/06143 | 7/1989 |
| WO | WO 93/15721 | 8/1993 |
| WO | W 94/06437 | 3/1994 |
| WO | WO 96/00047 | 1/1996 |
| WO | WO 96/03988 | 2/1996 |
| WO | WO 96/18411 | 6/1996 |
| WO | WO 98/56431 | 12/1998 |
| WO | WO 99/00149 | 1/1999 |
| WO | WO 00/69413 | 5/1999 |
| WO | WO 00/44306 | 9/1999 |
| WO | WO 00/33809 | 6/2000 |
| WO | WO 00/74650 A2 | 12/2000 |
| WO | WO 00/74650 A3 | 12/2000 |
| WO | WO 01/12247 A1 | 2/2001 |
| WO | WO 01/43726 | 6/2001 |

OTHER PUBLICATIONS

International Examination Search Report for PCT/US02/20802.*
Caterson, EJ, Nesti LJ, Li WJ, Danielson GK, Albert TJ, Vacaro, AR, Tuan RS Three-Dimensional Cartliage Formation by Bone Marrow-Derived Cells Seeded in Polylactide/Alginate Amalgam Dec. 5, 2002.
Funasaka Y, Sato H, Usuki A, Ohashi A, Kotoya H, Miyamoto K, Hill GG, Ichihashi M The Efficacy of Glycolic Acid for Treating Wrinkles: Analaysis USI Developed Facial Imaging Systems Equipped with Flourescent Illumination Aug. 27, 2002.
Hasirci V, Berthiaume F, Bondre SP, Gresser JD, Trantolo DJ, Toner M, Wise DL Express of Liver-Specific Functions by Rat Hepatocytes Seeded in Treated Poly(Latic-CO-Gllycolic) Asid Biodegradagle Foams Aug. 7, 2002.
Middleton, John C and Tipton Arthur J. Synthetic Buidegradable Poly as Medical Devices Mar. 1998.
Perugini, Paolo; Genta, Ida; Conti, Bice; Modena, Tiziana; Pavanetto, Franca Long-Term Release of Clodronate from Biodradable Microspheres Jul. 12, 2001.
Saito N, Okada T, Horiuchi J, Murakami N, Takahashi J, Nawata M, Ota H, Miyamoto S, Nozaki K, Takaoka K Biodegradable Poly-D,L-Lactic Acid-Polyethylene Glycol Block Copolymers as a BMP Delivery System for Inducing Bone 2001.
Santos AR Jr, Barbanti SH, Duek EA, Dolder H, Wada RS, Wada ML Vero Cell Growth and Differentiation on Poly(L-Lactic Acid) Membranes of Different Pore Diameter Jan. 25, 2001.
Tija JS, Aneskievich BJ, Moghe PV Substrate-Adsorbed Collagen and Cell Secreted Fibronectin CONC Induced Cell Migration on Poly(Lactic-Glycolide) Substrates Dec. 20, 1999.
Why Recombinant Human Collagen? www.fibrogen.com/collagen.
How Pepgen P-15 Mimics Autogenous Bone www.ceramed.com/pepgen_howmimics.htm.

* cited by examiner

BIODEGRADABLE INJECTABLE IMPLANTS CONTAINING GLYCOLIC ACID

This application is a continuation-in-part of application Ser. No. 10/002,283, filed on Dec. 5, 2001 now abandoned, entitled Biodegradable Injectable Implant, and claims priority to application Mexico PA/a2001/006732, filed Jun. 29, 2001.

FIELD OF THE INVENTION

This invention relates generally to the field of medical implants, and more specifically to biodegradable injectable implants and their methods of manufacture and use.

BACKGROUND OF THE INVENTION

With increasing age and/or as a consequence of certain diseases, the body's soft tissues, including collagen, muscle and fat can diminish, affecting appearance and/or diminishing function. With age, facial skin begins to show the effects of gravity, sun exposure and years of facial muscle movement, such as smiling, chewing and squinting. The underlying tissues that keep skin looking youthful and plump begin to break down, often leaving laugh lines, smile lines, crow's feet or facial creases over the areas where this muscle movement occurs. Areas surrounding the eyes, the temple and cheeks can become sunken and hollow in appearance. Internally, sphincter muscles that control many of the body's autonomic functions such as control of bladder function and gastric reflux diminish with age or disease. A number of medical filler products and techniques have been developed in an effort to correct these soft tissue deficits and restore form and function.

Soft-tissue fillers, most commonly injectable collagen or autologous fat, can help fill in tissue deficits, temporarily restoring a smoother, more youthful-looking appearance to the skin. When injected intra-dermally, these fillers plump up and add fullness to creased and sunken areas of the face. Injected collagen and fat are primarily used to improve the appearance of the skin's texture. They can help fill out deep facial wrinkles, creases and furrows, "sunken" cheeks, skin depressions and some types of scars. They are also used to add a fuller, more youthful look to the lips.

Deep folds in the face or brow caused by overactive muscles or by loose skin may be more effectively treated with cosmetic surgery, such as a facelift or browlift. Injectables are sometimes used in conjunction with facial surgery procedures, as injectables alone typically cannot change facial contours as can surgery.

Injectable bovine collagen received approval from the Food and Drug Administration in 1981 and was the first injectable filler product to be marketed in the United States. Allergic reaction is the primary risk of bovine collagen injections. Collagen injections should be used with caution in anyone with a history of allergies, and skin tests must be performed a month before the procedure to help determine if the patient is allergic to the substance. The collagen is injected using a fine needle inserted at several points along the edge of the treatment site. Since part of the substance is saline that will be absorbed by the body within a few days, the doctor will slightly overfill the area. Risks not necessarily related to allergies include infection, abscesses, open sores, skin peeling, scarring and lumpiness, which may persist over the treated area.

Collagen's longevity depends on the patient's lifestyle and physical characteristics as well as the part of the body treated. In general, the injected material is likely to disappear faster in areas that are more affected by muscle movement. The injections may need to be repeated at intervals of six months or longer to maintain the maximum cosmetic effect.

Collagen injections are also used as a treatment for stress urinary incontinence resulting from an incompetent sphincter mechanism. When implanted at the bladder neck, this filler acts as a soft bulking material augmenting the natural function of the sphincter mechanism, thus helping to restore urinary continence. However, patients may require retreatments to maintain continence.

The fat-injection procedure, known as autologous fat transplantation or microlipoinjection, involves extracting fat cells from the patient's abdomen, thighs, buttocks or elsewhere and reinjecting them beneath the facial skin. Fat is most often used to fill in "sunken" cheeks or laugh lines between the nose and mouth, correct skin depressions or indentations, minimize forehead wrinkles and enhance the lips.

Fat injections offer two advantages over bovine collagen. Fat cells are living cells which are transplanted from one area of the body to the site where they are being injected. Once the cells are implanted they continue to live and do not break down as quickly or dramatically as collagen protein does. Also, as the injected fat is taken from the patient's own body, there is no chance of an allergic reaction to the injection. Additionally, a relatively larger volume (50-100 cc) of fat cells may be transplanted, to augment sunken areas of the face, including the temples and cheeks.

The disadvantage of fat injection lies in the transplant process. Fat cells removed from one area and transplanted to another suffer damage in transit, and may not find adequate blood supply at the new site in order to survive. It is estimated that one half to two thirds of the fat cells transplanted to the new site die and are absorbed by the body. Therefore, not only must two to three times the amount of material needed be injected into the new site (in order to insure that one third of the required amount properly implants), but the procedure must be repeated two to three times in order to get the correct amount at the site. While fat injections offer longer lasting results than bovine collagen, the building up process takes longer. In addition, the disruption caused to the area treated (because of the larger amounts of material being injected) can cause swelling, bumpiness and discoloration for three to five days following each treatment.

Injectable products can also be prepared from the patient's own collagen and/or fibroblast cells, or from donated cadaver dermis. These materials function similarly to bovine products but avoid the risk of allergic reactions. Tissue donors are typically screened for absence of transmissible diseases; however, there is still some risk of transmitting viral diseases, including the human immune deficiency virus, with these products.

A number of other biological filler materials have been developed for facial-rejuvenation purposes. These include a porcine gelatin powder compound that is mixed with a patient's own blood and injected to plump up the skin (similar to injectable collagen) and non-animal derived hyaluronic acid (a substance found in all living organisms). The porcine preparations have uncertain results, high antigenicity due to utilization of animal-origin components, and risk of infection via blood application. In contrast, the hyaluronic acid products do not cause allergic reactions, but only last three to six months A number of synthetic products have been developed to overcome the inherent risks of biologics. Synthetic products may include non-biodegradable components, such as expanded polytetrafluoroethylene ("ePTFE"), polymethylmethacrylate ("PMMA"), polydimethylsiloxane ("PDMS"), and polyacrylamide. These materials do not readily break down in the body, and are therefore permanent. The body mounts a foreign body response to these polymers and forms a tight fibrous capsule around the material. Risks include the potential for these materials to migrate away from the injection site or to form an inclusion cyst at the site of encapsulation. The FDA has banned the use of liquid silicone in the U.S as a filler material, due to risks of migration and the potential to stimulate autoimmune disorders. Non-biodegradable injectables have been problematic in the treatment of urinary incontinence due to migration of the particles.

Another approach to providing a highly biocompatible synthetic filler material that will not migrate or encapsulate is to utilize biodegradable polymers. Biodegradation has been accomplished by synthesizing polymers that have hydrolytically unstable linkages in the backbone. Common chemical functional groups with this characteristic are esters, anhydrides, orthoesters, and amides. As of 1960, a wide range of biodegradable synthetic polymers had been developed, including a number of polymers derived from natural sources such as modified poly-saccharides (cellulose, chitin, and dextran) or modified proteins (fibrin and casein).

Some commercially available biodegradable devices are polyesters composed of homopolymers or copolymers of glycolic and lactic acid. Copolymers of glycolic acid with both l-lactic and d,l-lactic acids have been developed for both device and drug delivery applications. Medical devices comprised of these polymers have been used in wound closure (sutures, staples); tissue screws; orthopedic fixation devices (pins, rods, screws, tacks, ligaments); dental applications (guided tissue regeneration, such as products for gums and regeneration of maxillary bone); cardiovascular applications (stents, grafts); intestinal applications (anastomosis rings); and applications systems for repairing meniscus and cartilage. Some biodegradable polymers have also been used for cosmetic wrinkle patches. A widely used device is a copolymer of 90% glycolic acid and 10% l-lactic acid, developed by Ethicon as an absorbable suture material under the trade name Vicryl™. It absorbs within three to four months but has a slightly longer strength-retention time.

One of the first bioactive degradable polymers approved by the FDA was polylactide-co-glycolide acid. The implant based on this polymer is a slow dissolving injectable device for treatment of advanced prostate cancer. This device uses biodegradable a mixture of poly-glycolic acid (25%) and poly-lactic acid (75%) in the form of microspheres to gradually release an acetate for periods of up to 4 months, thereby avoiding the need for daily injections.

Other products have also been approved such as Pro-Lease® and Medisorb®, medical devices for the creation of slowly dissolving (from a few days up to several months) injectable products. Both technologies consist of injection methods comprised by bioactive molecules integrated in a matrix of poly-d,l-lactide-co-glycolide.

The use of biodegradable homopolymers and co-polymers of glycolic and lactic acid as injectable bulking implants is also disclosed in Australian patent no. 744,366. This patent discloses the purported use of polymeric lactic acid microspheres, having a mean diameter ranging from 5µ to 150µ, suspended in a gel. According to this invention, glycolic acid repeat units may be incorporated into a lactic co-glycolic acid polymer, to influence rates of degradation.

However, a major obstacle to the use of the aforementioned biodegradable polymers as an injectable bulking agent or implant is that, due apparently to surface charge characteristics, the polymeric particles tend to aggregate prior to and/or during clinical application. This aggregation causes the products to be difficult to mix following reconstitution—mixing often requiring an ancillary laboratory device, such as a Vortex mixer, to adequately suspend the microparticles. Further, despite aggressive mixing, the polymeric particles will frequently aggregate and obstruct and clog the syringe and needle, resulting in product wastage and/or suboptimal product injection. If injected in aggregated form, the polymers may not infiltrate within the interstitial spaces in the body or be assimilated and degraded thereby in an optimal manner. Instead, the aggregated particles may form hard, insoluble nodules at the injection site, causing edema and swelling, and requiring corrective medical intervention. In addition, products, based on polylactic acid, intended to replace fat loss at the temples and/or cheeks are expensive for this purpose, as the procedure requires several interventions—from three to six, 25 to 30 days apart.

Glycolic acid monomer (GA), in solution, is present in a wide number of cosmetic products and its use as a biomaterial has been suggested for pathologies related to an increase in corneocyte cohesion. GA has been used for acne prevention and treatment, as a component of topicals and injectable solutions. GA is also believed to reduce inflammation and optimize moistening. (It is documented that glycolic acid produces a 300% increase in skin moisture.) Despite its beneficial hydrating and intracellular diffusive properties, to date, no injectable implants have been prepared containing GA, alone or in combination with a polymeric filler.

In summary, the injectable products in the art are characterized by very short duration periods and/or allergic reaction. In addition, some of their components are dangerous and even lethal. Biodegradable polymeric implants that overcome some of these drawbacks suffer from further application complications such as needle clogging and nodule formation.

Thus, it would be desirable to design an implant that degrades very slowly over time; will not cause allergic reaction, rejection, or infection; does not require surgery to remove damaging residues or nodules; and will not migrate to the lungs, kidneys, liver, or other parts of the human body with deleterious results. For injectable applications, an implant having superior flow properties which avoids aggregation, needle clogging and nodule formation is. also desired.

SUMMARY OF THE INVENTION

The present invention solves many of the problems inherent in the art by providing a biocompatible, biodegradable, injectable bulking agent or implant that degrades slowly under biological conditions, is hypoallergenic, non-migratory, relatively inexpensive and simple to apply.

Aspects of the present invention encompass a biodegradable, injectable bulking agent or implant (also referred to herein as an "injectable") intended for use in reconstructive surgery to restore form and/or function to soft tissues altered by age, trauma, disease, or other defect comprising a solution containing glycolic acid monomer (referred to herein as "GA") and a particle suspension or emulsion of particles of a polymer containing or comprising lactic acid repeat units (also referred to herein as "PLA") as well as injectables in pre-activated solid form and related methods of production and use.

The injectables disclosed herein solve many problems inherent in the art. For example, the injectables of the present invention have flow properties superior to those available in the art. It is believed that the low molecular weight and hydrophilicity of GA (GA is highly soluble in water) inhibits aggregation and facilitates the flow of the denser PLA (higher molecular weight and having a hydrophobic surface), thereby avoiding clogging of the needle and the formation of nodules in the body. Thus, when added to a suspension of hydrophobic microparticles, the hydrophilic properties of GA in solution apparently overcomes the tendency for the hydrophobic particles to aggregate.

In addition, upon injection, the GA flows to and hydrates the upper layers of the dermis, renewing its elasticity and promoting a healthier skin, thereby enhancing physical appearance and improving the effect of the PLA microparticles. More specifically, as the PLA degrades, the body initiates a fibrosis response, resulting in increased deposition of collagen in the treated area. The filled area also reacts with the improved elasticity promoted by the action of GA. This characteristic allows PLA to work independently but complementarily with the GA.

The injectable implants disclosed herein are preferably biodegradable and biocompatible. The PLA and GA components are substantially, if not completely, degraded by the body. Polymers of lactic acid may be non-enzymatically hydrolized in vivo. The hydrolysis products may then be metabolized (for example, the lactic acid or other repeat units are typically metabolized) and excreted or excreted fully or partially intact. Although not wishing to be bound by any theory, it is believed that the PLA degrades via water diffusion followed by hydrolysis, fragmentation and further extension hydrolysis accompanied with phagocytosis, diffusion, and metabolization. This degradation process may typically take up to 12 months and is regulated by variables in the formulation and manufacturing of the injectables disclosed herein, including the features of polymers, excipients, and production method. The degradation by-products may be mainly expelled via normal respiration and excretion.

Thus, one aspect of the present invention relates to a biodegradable injectable bulking agent or implant comprising glycolic acid and a bio-compatible/bio-absorbable polymeric particle having a size that is small enough to be injected through a needle but large enough to avoid engulfment by macrophages.

The injectable implants disclosed herein are typically administered as a suspension of the polymeric particles in a pharmaceutically acceptable carrier with glycolic acid being present in the solution phase. However, it is envisioned that it may be desirable to store the injectables disclosed herein in a variety of physical forms to increase their shelf-life (for example, the freeze-dried form which has a shelf life of greater than 12 months), aid in shipment of product to customers, etc. Thus, aspects of the present invention include injectables which are in their activated form (i.e. ready for administration) as well as in pre-activated form (i.e. requiring additional manipulation or processing prior to administration). Thus, embodiments of the present invention encompass, but are not limited to, dehydrated, sterilized, typically freeze-dried powders, emulsions, suspensions, aqueous emulsions, and the like.

The bulking agents/injectables of the present invention include glycolic acid (GA). The concentration of GA will vary depending upon the particular application and the form of the implant. Typically, one of skill in the art is concerned with the concentration of the GA that will be administered to the patient. For example, when the injectable implant is in the form of a suspension of particles in a pharmaceutically acceptable carrier (e.g., an activated form), the GA may typically be present in a concentration of from about 1.8 mcg to about 18.2 mcg GA per 100 ml of the pharmaceutically acceptable carrier (or from about 0.0018% to about 0.0002% by weight), from about 11 mcg to 14 mcg per 100 ml of the pharmaceutically accentable carrier, and preferably from about 12 mcg to 13 mcg per 100 ml of the pharmaceutically acceptable carrier, or about 12.7 mcg per 100 ml of the pharmaceutically acceptable carrier. However, when the implant is in a pre-activated solid form, the GA may typically comprise from about 0.002% to about 0.02% by weight, prefereably about 0.014% by weight.

The size and shape of the polymeric particles may vary depending on the intended application. However, the polymeric particles included in the injectables typically have a diameter of from 20μ to about 120μ, preferably from about 40μ to about 80μ, and more preferably have a mean diameter of from about 50μ to about 70μ, or from about 55 to about 65μ, or about 60μ. Although the shape of the particles may vary widely depending upon the intended application and various production parameters, a preferred shape is substantially spherical (often referred to in the injectable art as a microsphere). The polymeric particles having the desired shape and size are preferably made by pulverizing the polymer to a powder; and cold micronizing the powder to the desired shape and size.

The polymeric particles comprise a polymer which contains a substantial amount of lactic acid repeats units (typically from 10 to 100% lactic acid repeat units by weight, preferably from 50%, 60%, 70%, 80% or 90% up to about 100%. Thus, embodiments of the present invention encompass implants wherein the polymer comprises homopolymers of lactic acid, such as poly-l-lactic acid or poly-d,l-lactic acid, and co-polymers of lactic acid.

The co-polymers encompassed in the present invention may have varying compositions depending upon the intended application and production parameters. For example, co-polymers of lactic acid and glycolic acid may be employed. Further, homo-and co-polymers of lactic acid may be employed which incorporate different repeat units (such as lactones) having a desired functionality. Thus, polymers containing repeat units which allow for crosslinking or which increase or decrease the rate of degradation of the polymer or affect the metabolism of the hydrolysis products produced by degradation or which bind preferentially to drugs or other bioactive compounds that may be administered at the site of the injection of the implant may be employed. In addition, homo- and co-polymers of lactic acid may be functionalized or modified after their synthesis and/or before, during or after their processing to discrete particles to incorporate additional chemical groups, moieties or functionalities or to modify the surface or other properties of the polymer or particles thereof.

The polymer is preferably substantially free of impurities, and preferably employed in a highly-purified form.

The properties of the polymer employed with injectables disclosed herein vary widely depending upon the intended application and composition and are typically not critical as long as one of skill in the art can form biodegradable, biocompatible hydrophobic particles therewith. Thus, for injectable applications, the polymeric particles should be suitable for injection through a suitably-sized syringe. Typically, the polymers employed herein exhibit an intrinsic viscosity of from about 3.0 to about 4.5 dl/g, more typically of from about 3.5 to about 3.8 dl/g or from about 3.60 to about 3.75 dl/g. The polymers employed herein may also have a density of from about 1.0 to about 1.5 kg/l, preferably about 1.24 kg/l, and a melting point ranging from about 170° to about 200° C.

The molecular weight as determined by viscosity of the polymer will typically be in the range of from about 100,000 to about 250,000 Daltons, preferably from about 150,00 to about 200,000 or 220,000 Daltons, and more preferably from about 165,00 to about 180,000 Daltons or about 172,000 Daltons.

The implants disclosed herein may include varying amounts of polymeric particles and may typically include in the activated form from about 30 mg to about 40 mg of polymer per 100 ml of the pharmaceutically acceptable carrier, preferably from about 36 mg to about 37 mg of polymer per 100 ml of the pharmaceutically acceptable carrier. However, when the implant is in a pre-activated solid form, the polymeric particles may typically comprise from about 36% to about 45% by weight of the solid, preferably from about 40 to about 41% by weight.

An embodiment of the present invention also encompasses an implant which further comprises a gelling agent. The gelling agent may typically comprise a cellulose derivative, such as hydroxypropylmethylcellulose or carboxymethylcellulose, or a pharmaceutically acceptable acid or ester. Exemplary pharmaceutically acceptable acid or ester gelling agents include synthetic hyaluronic acids, lactic acid esters, sodium carmellose, and caproic acid esters. The gelling agent, if present, is typically present in the activated implant in a concentration of from about 0-10% by weight, more typically from about 1% to about 5% by weight, with from about 2% to about 3% by weight being preferred. The pre-activated lyophilized powder form for the injectable may comprise from about 0-40%, preferably from about 20 to about 30%, or from about 22 to about 26%, by weight gelling agent, if any.

Injectables disclosed herein may also contain a surfactant, such as polyoxyethylene sorbitan, a polysorbate or pluronic acid, with polyoxyethylene sorbitan monooleate, polyoxyethylene sorbitan trioleate, polyoxyethylene sorbitan monostearate, polyoxyethylene sorbitan tristearate, polyoxyethylene sorbitan monopalmitate, and polyoxyethylene sorbitan monolaurate being preferred.

Other embodiments encompass injectables which further comprise a cryoprotecting agent. Suitable cryoprotecting agents include sugars and carbohydrates, for example, d-mannitol, lactose, sucrose, fructose, and dextran.

In other embodiments, the inclusion of stabilizers into the injectables disclosed herein (such as buffering agents—e.g. dibasic and monobasic phosphates and citrates) permit the safe preservation for 30 to 45 days once the injectable product is reconstituted, or activated, with water or other pharmaceutically acceptable carrier. (A similar product, once activated, has a life of no more than 72 hours.)

Thus, the injectable implants of this invention may also include a buffering agent or system. The buffering agent(s) may be any pharmaceutically acceptable buffer, including but not limited to phosphate and citrate buffers. The buffering agent, if present, may typically be present in the activated form in a concentration of from about 0-0.1 mg per 100 ml of the pharmaceutically acceptable carrier, or from about 0.08 mg to about 0.1 mg per 100 ml of the pharmaceutically acceptable carrier, with about 0.09 mg per 100 ml of suspension being preferred. The lyophilized powder form for the injectable may typically comprise from 0-0.2% by weight, or from about 0.09% to about 0.11% by weight buffering agent, if any.

An aspect of the present invention also encompasses injectable implants that comprise a medicament. This medicament may be any bioactive composition, pharmaceutical, drug or compound which one desires to administer to the site of the injection of the implant. For example, the medicament may comprise an anesthetic to decrease the pain or discomfort associated with injecting the implant or a composition that facilitates the integration of the polymer or decreases the trauma to the injection site. Exemplary anesthetics include but are not limited to lidocaine, xylocaine, novocaine, benzocaine, prilocaine, ripivacaine, and propofol. Typically the anesthetic will be used with an aqueous base and thus will be mixed with the pharmaceutically acceptable carrier and added to the inactive form of the injectable prior to administration.

Other medicaments that can be employed in the injectables disclosed herein include peptides, a tissue regeneration agent, an antibiotic, a steroid, fibronectin, a cytokine, a growth factor, an analgesic, an antiseptic, alpha-, beta, or gamma-interferon, erythropoietin, glucagons, calcitonin, heparin, interleukin-1, interleukin-2, filgrastim, cDNA, DNA, proteins, peptides, HGH, luteinizing hormone, atrial natriuretic factor, Factor VIII, Factor IX, and follicle-stimulating hormone.

An embodiment also encompasses the implant in the form of a suspension of the polymeric particles in a pharmaceutically acceptable carrier. Exemplary pharmaceutically acceptable carriers include but are not limited to water, saline, starch, hydrogel, polyvinylpyrrolidone, polysaccharide, hyaluronic acid ester, and plasma, with water being preferred.

Other embodiments encompass the injectables disclosed herein in a ready for use prefilled sterile syringe; in a vial in the form of a sterile suspension; in the form of a lyophilized powder; and in a two-compartment prefilled syringe, wherein one compartment contains a powder, preferably freeze-dried, and the other compartment contains a pharmaceutically acceptable carrier.

The implants disclosed herein may optionally be sterilized by gamma or E-beam irradiation or exposure to ethylene oxide gas.

Another embodiment encompasses a biodegradable, injectable implant comprising glycolic acid and particles comprised of polylactic acid (including but not limited to poly-1-lactic acid or poly-d,1-lactic acid, and co-polylactide-polyglycolide), wherein the particles have a mean diameter of from about 40µ to about 80 µ.

A further embodiment encompasses a biodegradable, injectable implant comprising:
  a) glycolic acid;
  b) particles of polylactic acid, wherein the particles have a mean diameter of from about 40µ to about 80µ;
  c) a gelling agent;
  d) a surfactant;
  e) a cryoprotecting agent; and
  f) a buffering agent.

The processes for producing the injectable implants disclosed herein also represents a significant advance over the art. More specifically, the disclosed separation, washing and drying techniques disclosed herein avoid several transfer and contaminating steps employed in the art, thereby facilitating an aseptic process—a problem that has plagued the manufacture and supply of analogous products. The processes of the present invention also save time, which considerably lowers production cost.

Thus, an aspect of the present invention encompasses a method of making a biodegradable, injectable implant comprising:
a) pulverizing a polymer comprising lactic acid repeat units to a first powder;
b) cold micronizing the first powder to form particles having a mean diameter of from about 20µ to about 120µ, preferably from about 40µ to about 80µ;
c) forming an emulsion or suspension comprising the particles;
d) obtaining a solution which comprises glycolic acid;
e) mixing the emulsion and solution during heating to obtain an aqueous slurry;
f) drying the aqueous slurry, typically under vacuum and a stream of dry air, to obtain a second powder; and
g) lyophilizing the second powder.

The injectables so prepared may also optionally include gelling agents, surfactants, cryoprotecting agents, and buffering agents.

An aspect of the invention also encompasses the further step of comprising forming a suspension of the second powder in a pharmaceutically acceptable carrier, such as water, saline, starch, hydrogel, polyvinylpyrrolidone, polysaccharide, hyaluronic acid ester, or plasma.

A further aspect of the present invention encompasses a method of using the injectable bulking agents and implants disclosed herein to replace facial fat loss (lipoatrophy), for example, to provide volume in areas of the patient's soft tissues which suffer from fat, collagen or muscle loss for reasons of old age or disease.

Another aspect of the present invention encompasses a method of using the injectable bulking agents and implants disclosed herein for the treatment of a sphincter deficiency, such as a deficiency of the urinary or pyloric or lower esophageal sphincter, or for treatment of erectile dysfunction. For example, in cases of incontinence the bulking agent may be injected endoscopically at the sphincter controlling the bladder, whereas to treat acid reflux, the bulking agent may be endoscopically injected at the duodenal sphincter.

The injectable implants disclosed herein may also be used to treat wrinkles and scars by injection at the site of the wrinkle or scar or to treat certain conditions of the vocal cords or to support tendons by injection at those sites.

Thus, an aspect of the invention encompasses a method for soft tissue augmentation comprising injecting a mammal, such as a human at an injection site in need of such soft tissue augmentation a bulking agent comprising glycolic acid and polymeric particles comprising lactic acid repeat units, wherein the particles have a mean diameter of from about 20µ to about 120µ, preferably from 40µ to about 80µ.

The injection site may be a congenital anomaly, a scar, such as a chicken pox or acne scar, or a wrinkle. Further, the bulking agent may be used to augment facial fat loss in the human or to treat a sphincter deficiency. When used to treat a sphincter deficiency, the injection site may be urethral or periurethral tissue or tissue at or proximal to the pyloric or lower esophageal sphincter. The injection site may also be tissue defining a vocal cord.

If the injectables used include a medicament or other component in sufficient volume and/or that is readily absorbed by the body, it may be desirable to overfill the injection site with the bulking agent/implant, thus providing sufficient filler at this site after the medicament or other component is absorbed or otherwise integrated into or dispersed to the site and surrounding tissue.

It has also been surprisingly found that injection of GA alone has a remarkable re-hydrating effect of the skin. Therefore, an aspect of the present invention encompasses a method for improving the appearance of a wrinkle on a human comprising injecting glycolic acid into the human at the wrinkle.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
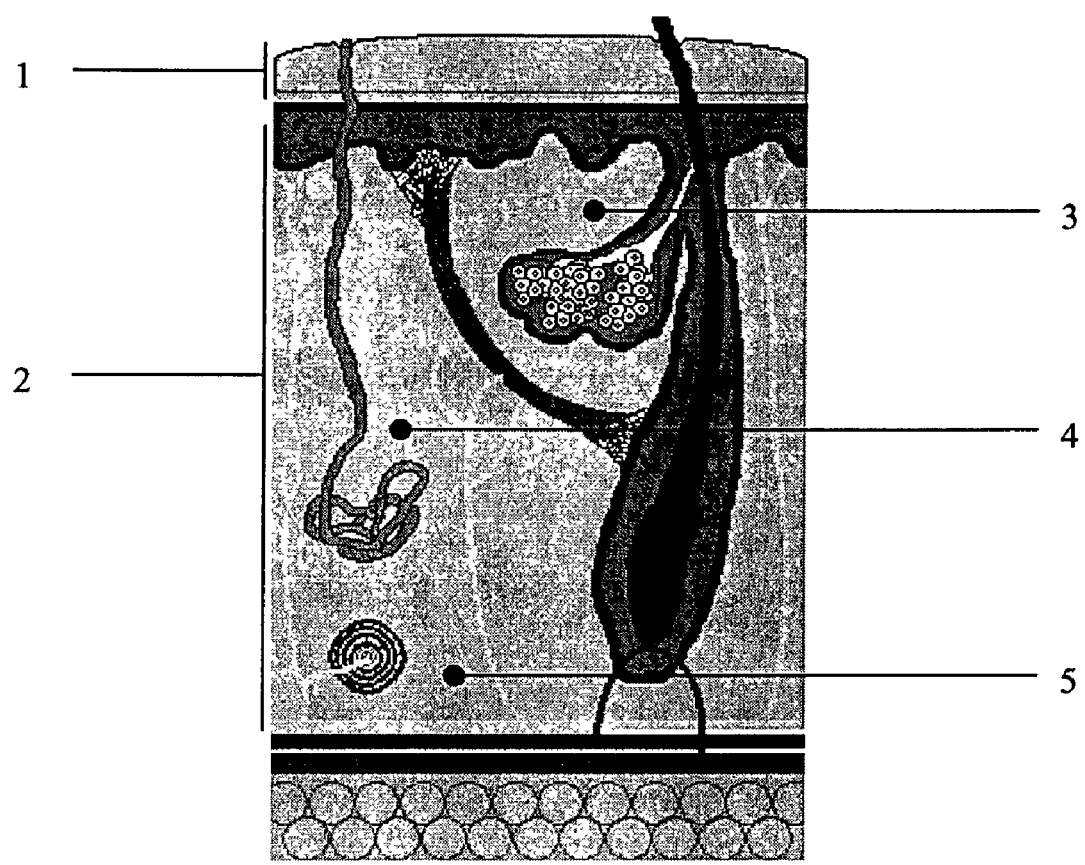
FIG. 1 illustrates typical injection sites in the dermis for cosmetic and lipodystrophy methods.

1 Biodegradable, Injectable Bulking Agents and Implants

The biodegradable, injectable implants and bulking agents disclosed herein comprise bioactive molecules of glycolic acid (GA) and polymers containing lactic acid repeat units (also referred to herein as PLA). The PLA preferably forms a hydrophilic matrix in a microsphere-based delivery system, designed to assure the stability of GA and PLA molecules and the desired profile of a safe implant. Both GA and the preferred PLA compositions have been scientifically proven to be innocuous, biodegradable, biocompatible and bioabsorbable medical components, devoid of side effects or allergic reactions.

It is believed that interaction from the microspheres is governed by diffusion of the bioactive molecule through the microsphere and by biodegradation of the polymer. The process is modulated through a number of formulation and manufacture variables, including glycolic acid, the addition of gelling, cryoprotecting and tenso-active agents, and a pH stabilizer.

The injectables are typically packaged in vials as a freeze-dried, free-flowing powder. Once activated with distilled injectable water or other pharmaceutically acceptable carrier, the gelatinous (suspension) fluid may be implanted by subcutaneous injection.

Therefore, an aspect of the present invention encompasses biodegradable, injectable bulking agents and implants (herein referred to as "injectables") comprising glycolic acid ("GA") monomer and biocompatible, biodegradable particles of polymers comprising lactic acid ("PLA"). The injectables typically comprise PLA particles, preferably microspheres, having a diameter ranging primarily from about 20µ to about 120µ, typically from about 40µ to about 80µ, preferably with a mean diameter of approximately 60µ. It is preferred to employ microspheres having diameters larger than about 40µ to minimize immediate phagocytosis by macrophages and intra-capillary diffusion. Diameters smaller than 80µ are preferred to minimize the granular texture of the injectable and facilitate the free flow of the injectable through intradermal needles (typically 26-28 gauge).

In some embodiments, the injectables may also comprise gelling agents, such as cellulose derivatives, hydroxypropylmethylcellulose ("HPMC"), or carboxymethylcellulose ("CMC"); surfactants or tensoactive agents, such as polyoxyethylene sorbitan monooleate (Tween 80™) or pluronic acid; cryoprotecting agents, such as apirogen mannitol (d-mannitol), dextran, and others known to those of ordinary skill in the art, and buffering agents to stabilize pH, such as basic sodium phosphate and citrate buffers. The injectables may also include a medicament, such as a local anesthetic to minimize stinging and burning during the injection procedure.

Interaction among particles is affected by precise manufacturing/formulation variables—including characteristics of polymers and excipients (inert substances).

The injectable implants disclosed herein are typically administered as a suspension of the polymeric particles with the GA being present in the solution phase. However, it may be desirable to store the injectables disclosed herein in a variety of physical forms, including both activated form (i.e. ready for administration) and pre-activated form (i.e. requiring additional manipulation or processing prior to administration).

The activated form is typically a suspension of the polymeric particles in a pharmaceutically acceptable carrier. Exemplary pharmaceutically acceptable carriers include but are not limited to water, saline, starch, hydrogel, polyvinylpyrrolidone, polysaccharide, hyaluronic acid ester, or plasma, with water being preferred. The pre-activated form is typically a dried powder lacking the pharmaceutically acceptable carrier and/or one or more other ingredients that are soluble in the pharmaceutically acceptable carrier (such as the glycolic acid, buffering agent(s), cryoprotecting agent, gelling agent, surfactant, medicament, anesthetic, etc.)

The injectable of the present invention may be typically provided in a ready for use prefilled sterile syringe, or in a vial in the form of a sterile suspension. In preferred embodiments, the injectable may be in the form of a lyophilized powder to facilitate sterilization and storage. In these embodiments, the end user adds water or other pharmaceutically acceptable carrier and/or additional components prior to injection. The injectable may also be provided in a two-compartment prefilled syringe, one containing the freeze-dried powder and the other containing water or other pharmaceutically acceptable carrier. If reconstituted extemporaneously, e.g., by double distilled water, for injectable preparations, the gel-like fluid (suspension) may then be applied by intradermal or subcutaneous injection. The viscosity of the suspension is inversely proportional to temperature.

The biodegradable polymers used must have proper mechanical properties to comply with the medical object of the particular application. They should not cause significant swelling or have toxic effects and are preferably substantially metabolized upon degradation.

The relationship between the polymer composition and the mechanical and degradation properties of the materials may be important for device or drug release activity. Generally, the mechanical properties and the time of degradation should match the needs of the application. The preferred polymer for a particular application should be configured so that it:

Has mechanical properties that match the application, remaining sufficiently strong until the surrounding tissue has healed;

Does not invoke an inflammatory or toxic response;
Is metabolized in the body after fulfilling its purpose, leaving no trace;
Is easily processable into the final product form;
Demonstrates acceptable shelf life; and
Is easily sterilized.

The factors affecting the mechanical performance of biodegradable polymers include monomer selection, initiator selection, process conditions, and the presence of additives. These factors in turn influence the polymer's hydrophobicity, crystallinity, melt and glass-transition temperatures, molecular weight, molecular-weight distribution, end groups, sequence distribution (random versus blocky), and presence of residual monomer or additives.

Once implanted, a biodegradable bulking agent or implant should maintain its mechanical properties until it is no longer needed and then be absorbed and excreted by the body, leaving little or no trace. Simple chemical hydrolysis of the hydrolytically unstable backbone is the prevailing mechanism for the degradation of the polymers employed herein. This occurs in two phases. In the first phase, water penetrates the bulk of the PLA particle, preferentially attacking the chemical bonds in the amorphous phase and converting long polymer chains into shorter water-soluble fragments. Because this occurs in the amorphous phase initially, there is a reduction in molecular weight without a loss in physical properties, since the polymer matrix is still held together by the crystalline regions. The reduction in molecular weight is soon followed by a reduction in physical properties, as water begins to fragment the particle. In the second phase, enzymatic attack and metabolization of the fragments occurs, resulting in a rapid loss of polymer mass. This type of degradation—when the rate at which water penetrates the particle exceeds that at which the polymer is converted into water-soluble materials (resulting in erosion throughout the device)—is called bulk erosion. Commercially available synthetic devices and sutures degrade by bulk erosion.

A second type of biodegradation, known as surface erosion, occurs when the rate at which the water penetrates the particles is slower than the rate of conversion of the polymer into water-soluble materials. Surface erosion results in the device thinning over time while maintaining its bulk integrity. Polyanhydrides and polyorthoesters are examples of materials that undergo this type of erosion—which typically occurs when the polymer is hydrophobic, but the chemical bonds are highly susceptible to hydrolysis. In general, this process is referred to in the literature as bioerosion. The degradation-absorption mechanism is the result of many interrelated factors, including:

The chemical stability of the polymer backbone;
The presence of catalysts, additives, impurities, or plasticizers; and
The geometry of the device.
Factors that accelerate polymer degradation include:
More hydrophilic backbone;
More hydrophilic endgroups;
More reactive hydrolytic groups in the backbone;
Less crystallinity;
More porosity; and
Smaller device size.

Particles incorporating biodegradable polymeric lactic acid are preferably not subjected to autoclaving, and are optionally sterilized by gamma or E-beam irradiation or by exposure to ethylene oxide (EtO) gas. There are certain disadvantages, however, to both irradiation and EtO sterilization. Irradiation, particularly at doses above 2 Mrd, can induce significant degradation of the polymer chain, resulting in reduced molecular weight as well as influencing final mechanical properties and degradation times. Because the highly toxic EtO can present a safety hazard, great care must be taken to ensure that all the gas is removed from the device before final packaging. The temperature and humidity conditions should also be considered when submitting devices for sterilization. Temperatures must be kept below the glass-transition temperature of the polymer to prevent the part geometry from changing during sterilization. If necessary, parts can be kept at 0° C. or lower during the irradiation process.

2 Chemical Components of the Injectables 2.1 Glycolic Acid ("GA")

The injectables of the present invention comprise glycolic acid ($HOCH_2COOH$). Glycolic acid is a moderately strong organic acid and is the first member of the alphahydroxy acid series. GA is very soluble in water, methanol, ethanol, acetone, acetic acid, and ethyl acetate, but poorly soluble in diethyl ether, and very poorly soluble in hydrocarbon solvents. At high concentrations, free glycolic acid exists in equilibrium with low molecular weight, polyester oligomers. Upon dilution, neutralization, etc., these components revert to free glycolic acid.

GA for use in the present invention may be obtained commercially or produced by methods well known by those of skill in the art. Preferably, purified GA suitable for use in biomedical applications is employed.

While not wishing to be bound by any theories, it is believed that the glycolic acid serves many purposes in the injectables of the present invention. First, it is believed to promote the ease of flow of the hydrophobic PLA microparticles through the fine intradermal needles employed, thereby avoiding clogging—a significant problem with known polylactic acid injectable implants. Presumably, the GA which is highly hydrophilic, is dissolved in the fluid phase (which is typically aqueous). Second, the glycolic acid may facilitate rapid diffusion of the implant microparticles into the injection site, preventing the formation of nodules—another complication with known polylactic acid injectables.

The glycolic acid may also facilitate infiltration of the implant and hydration of the injected area thereby also reducing inflammation (as a result of tissue trauma caused by the necessary injection procedure). In this regard, the hydrophilic glycolic acid easily diffuses throughout the intracellular aqueous phase without the need for plasmatic retinoid proteins. GA may also serve as a keratin regulator, inhibiting cohesion of corneocytes growing on the cornea layer mantles. Thus, the GA also promotes increased flexibility, hydration, and turgidity of the outer layers of the skin. GA degradation at the injection presumably occurs in a few weeks.

All of these factors facilitate the microparticle implant's infiltration, assimilation and ultimate degradation and promote a healthier epidermis in support of the tissue filling/contouring purpose of the injectable.

For embodiments of the present invention wherein the injectables are in the form of a suspension of PLA particles, the GA may typically be dissolved in a pharmaceutically acceptable carrier, preferably water.

The concentration of the GA in the injectable will vary depending upon the intended application, particulars related to the PLA composition and particles, and the identity of the other components of the injectable, if any. Typically, one of skill in the art is concerned with the concentration of the GA that will be administered to the patient, that is, the concentration of GA in the injectable implant in its activated form. Thus, when the injectable implant is in the form of a suspension of particles in a pharmaceutically acceptable carrier (e.g., an activated form), the GA may typically be present in a concentration of from about 1.8 mcg to about 18.2 mcg GA per 100 ml of the pharmaceutically acceptable carrier (or from about 0.0018% to about 0.0002% by weight), and preferably from about 12 mcg to 13 mcg per 100 ml of the pharmaceutically acceptable carrier, or about 12.7 mcg per 100 ml of the pharmaceutically acceptable carrier.

However, it is contemplated one may desire to make, store, and transport the injectable implants disclosed herein in a pre-activated solid form. When the implant is in a pre-activated solid form, the GA may typically comprise from about 0.002% to about 0.02% by weight, preferably about 0.014% by weight.

2.2 Polylactic Acid ("PLA")

The injectables of the present invention comprise a polymer containing lactic acid repeat units, PLA. While not wishing to be bound by any theories, it is believed that the PLA serves many purposes in the injectables of the present invention. First, the PLA serves as the bulking or tissue contouring agent. The PLA also facilitates an enzymatic process while the PLA is being degraded or assimilated in the patient's body. During the polymer's assimilation, a limited tissue response occurs which is the body's reaction to the presence of a foreign body. This triggers fibrosis (a neocollagenesis process) to replace the lost tissue mass and/or bulk the areas where the product is so infiltrated. The biocompatibility of the PLA makes it a superior support for cellular growth and tissue regeneration.

2.2.1 PLA Composition and Properties

The PLA may comprise any polymer of lactic acid, that is, a polymer which contains more than a nominal number of lactic acid repeat units. Thus, the PLA employed in the disclosed injectables may typically contain a substantial amount of lactic acid repeats units (typically from 10 to 100% lactic acid repeat units by weight, and preferably from 50%, 60%, 70%, 80% or 90% up to about 100%).

Polymers are high molecular weight molecules made up of low molecular weight repeating units called monomers. The process of joining monomers to produce polymers is called polymerization.

Polylactic acid is a poly-α-hydroxyacid containing repeat units derived from lactic acid ($HOCH(CH_3)COOH$). Polylactic acid may be present as one of several different optical isomers or mixtures thereof, such as L, D, meso, and racemic (50% L and 50% D) isomers. A typical range of properties for L-PLA and L,D-PLA are as follows:

|   | Molecular Mass (Kda) | % Crystallinity | Viscosity N (dl/g) | Density P (g/cm$^3$) |
|---|---|---|---|---|
| L-PLA | 50-756 | 15-74 | 0.61-8.2 | 1.25 |
| LD-PLA | 21-550 | 0 (amorphous) | 0.25-2.01 | 1.29 |

Various forms of polylactic acid are commercially available or may be prepared by methods well known to those of skill in the art, such as polymerization of lactide dimers (Kronenthal, 1975). Thus, in some preferred embodiments, L-lactide may be polymerized at elevated temperatures using stannous octoate as a catalyst/initiator and lauryl alcohol (dodecanol) as a co-initiator. After polymerization and purification (to remove residual monomer), the polymer may be ground to small granules.

Poly(l-lactide) is a biodegradable, immunologically inactive, biocompatible, and bioabsorbable synthetic polymer that belongs to the family of aliphatic polyesters. Degradation occurs naturally when in contact with live tissue or an aqueous environment by hydrolysis to lactic acid which may be further biodegraded.

Degradation starts by water diffusion (initially at the more amorphous zones) followed by hydrolysis, material fragmentation and, finally, a more extensive hydrolysis along with phagocitosis, diffusion, and metabolization. The degradation by-products are eliminated, essentially, via the respiratory tract.

The PLA is degraded by nonspecific hydrolysis. Degradation may be slower as crystallinity, L-PLA content or the molecular weight is increased or as repeat units that are less susceptible to hydrolysis or allow for the formation of crosslinks are incorporated. Thus, the resorbability time may be adjusted by changing these properties.

The mechanical and pharmaceutical properties of assimilation also depend on the chemical make-up of the polymer and its molecular weight. For example, a crystalline formation (mostly made up of L-lactide) and a high molecular weight (>100,000 Dalton) may allow for extended assimilation (slightly over a year). Different formulas allow regulation of the assimilation speed (radical add-ons to chains).

Thus, embodiments of the present invention encompass implants wherein the polymer comprises homopolymers of lactic acid, such as poly-l-lactic acid or poly-d,l-lactic acid, and co-polymers of lactic acid.

The co-polymers encompassed in the present invention may have varying compositions depending upon the intended application and production parameters. For example, co-polymers of lactic acid and glycolic acid may be employed. Further, homo-and co-polymers of lactic acid may be employed which have incorporated different repeat units (e.g., lactones) having a desired functionality. Thus, for example, repeat units which allow for crosslinking or which are more or less susceptible to hydrophilic attack or which bind preferentially to drugs or other compounds that may be administered at the site of the injection of the implant may be employed.

The polymer is preferably substantially free of impurities, and preferably employed in a highly-purified form.

The properties of the polymer employed in the injectables disclosed herein vary widely depending upon the intended application and are typically not critical as long as one of skill in the art can form hydrophobic particles therewith. Thus, for injectable applications, the polymeric particles should be suitable for injection through a suitably-sized syringe. The intrinsic viscosity for the PLA which may be important to certain aspects of the present invention is typically from about 3.0-4.5 dl/g (measured in chloroform at 25° C.), preferably from about 3.2-4.2 dl/g, more preferably from about 3.5 or 3.6 to about 3.8 dl/g, and even more preferably from about 3.62-3.75 dl/g or around 3.7 dl/g. The PLA employed may typically have a density of from about 1.0 to about 1.5 kg/l, and preferably has a density of about 1.24 kg/l.

The molecular weight as determined by viscosity of the polymer will typically be in the range of from about 100,000 to about 250,000 Daltons, preferably from about 150,000 to about 200,000 or 220,000 Daltons, or from about 160,000 or 165,000 to 180,000 Daltons. The melting point range is usually from about 170°-200° C. (as determined by differential scanning calorimetry ("DSC"), 10° C./min), and preferably from 175°-195° C.

The implants disclosed herein may include varying amounts of polymeric particles and may typically include in the activated suspension from about 30 mg to about 40 mg of polymer per 100 ml of the pharmaceutically acceptable carrier, preferably from about 36 mg to about 37 mg of polymer per 100 ml of the pharmaceutically acceptable carrier. When the implant is in a pre-activated solid form, the polymeric particles may typically comprise from about 36% to about 45% by weight, preferably from about 40 to about 41% by weight.

In preferred embodiments, poly-L-lactide is employed, preferably PURASORB® PL from PURAC and polymer poly (L-lactide), manufactured by Birmingham Polymers, Inc., Birmingham, Ala., U.S.A. For biomedical applications, purified and/or highly purified polylactic acid is preferred such that residual solvent is <0.01% and residual monomers <0.1%.

2.2.2 Preparation of PLA Particles

The PLA particles that may be employed in the injectables of the present invention typically are prepared by processing the PLA particles to an appropriate size and/or shape. Thus, in some embodiments, the PLA may be subjected to a two-stage grinding process. In the first step, the PLA is pulverized and in the second step the solid is cold micronized (e.g., at −80° C.) to obtain particles having a diameter of the appropriate size, typically from about 20μ to about 120μ or from about 40μ to about 80μ, and preferably having a mean diameter of from about 40μ, 50μ, or 55μ to about 65μ, 70μ or 80μ and/or having a mean diameter of about 60μ. This process is particularly preferred for embodiments employing crystalline PLA.

Although the shape of the particles may vary widely depending upon the intended application and various production parameters, a preferred shape is substantially spherical (often referred to in the injectable art as a microsphere).

2.3 Gelling Agents

For some embodiments, the injectables may be administered as a gel or relatively homogenous suspension of PLA particles. The injectables may also comprise a gelling agent and water or other pharmaceutically acceptable carrier for ease of injection. Gelling agents are well known in the art and are ingredients that aid gel formation. Suitable gelling agents include, but are not limited to, cellulose derivatives, such as hydroxypropylmethylcellulose ("HPMC") and carboxymethylcellulose ("CMC"), synthetic hyaluronic acids, lactic acid esters, sodium carmellose, caproic acid esters, and the like, with HPMC being preferred.

The concentration of the gelling agent in the activated form will vary depending upon the intended application, and particulars related to the PLA composition and particles, identity of the gelling agent, etc., but, may typically vary from about 0-10% by weight, more typically from about 1% to about 5% by weight, with from about 2% to about 3% by weight being preferred. The pre-activated powder form for the injectable may typically comprise from about 0-40%, preferably from about 20% to about 30%, or from about 22% to about 26%, by weight gelling agent, if any. The amount of gelling agent is typically chosen to obtain a suspension having the desired flow properties, i.e., not too thick or gelatinous or too liquid.

2.4 Cryoprotecting Agent

For some embodiments, the injectables may also contain a cryoprotecting agent. A cryoprotecting agent is a chemical which inhibits or reduces the formation of damaging ice crystals in biological tissues during cooling. Suitable cryoprotecting agents include, but are not limited to sugars and carbohydrates, such as d-mannitol, lactose, sucrose, fructose, and dextran, with d-mannitol being preferred. The concentration of the cryoprotecting agent in the activated suspension to be injected will vary depending upon the intended application, and particulars related to the PLA composition and particles, identity of the cryoprotecting agent, but will vary from about 0-50 mg per 100 ml of suspension, typically from about 27 to about 35 mg per 100 ml of the pharmaceutically acceptable carrier, with concentrations in the range of from about 29 to about 32 mg per 100 ml of the pharmaceutically acceptable carrier being preferred. The lyophilized powder form for the injectable may typically comprise 0-45% by weight, or from about 30% to about 40% or from about 33% to about 38% or about 35% by weight, cryoprotecting agent, if any.

2.5 Surfactants or Tensoactive Agents

For some embodiments, the injectables may also contain a surfactant or tensoactive agent. A surfactant is a chemical that reduces the surface tension in a solution, allowing small, stable bubbles to form. Suitable surfactants include, but are not limited to, polysorbates, such as polyoxyethylene sorbitans, or pluronic acid, preferably polyoxyethylene sorbitan monooleate, polyoxyethylene sorbitan trioleate, polyoxyethylene sorbitan monostearate, polyoxyethylene sorbitan tristearate, polyoxyethylene sorbitan monopalmitate, or polyoxyethylene sorbitan monolaurate, with polyoxyethylene sorbitan monooleate (Tween 80™), polyoxyethylene sorbitan monostearate (Tween 60™), and polyoxyethylene sorbitan monolaurate (Tween 20™) being preferred, and polyoxyethylene sorbitan monooleate(Tween 80™), being even more preferred.

In these embodiments, the surfactant is typically present in the activated form of the implant in a concentration of from 0-0.03% by weight, more typically from about 0.019% to about 0.024%, preferably about 0.021%. The lyophilized powder form for the injectable may comprise from 0-0.3%, preferably from about 0.22% to about 0.27% or about 0.24% by weight surfactant, if any.

2.6 Buffering Agents

For some embodiments, the injectables may also contain a buffering agent. A buffering agent is a chemical compound or compounds that is added to the solution to allow that solution to resist changes in pH as a result of either dilution or small additions of acids or bases. Effective buffer systems employ solutions which contain large and approximately equal concentrations of a conjugate acid-base pair (or buffering agents). The buffering agents employed herein may be any such chemical compound(s) which is pharmaceutically acceptable, including but not limited to salts (conjugates acids and/or bases) of phosphates and citrates. The concentration of the buffering agent(s) will depend upon its strength, the composition of the implant and its intended purpose, but may typically range in the activated form from about 0-0.1 mg per 100 ml of the pharmaceutically acceptable carrier, or from about 0.08 mg to about 0.1 mg per 100 ml of the pharmaceutically acceptable carrier, with about 0.09 mg per 100 ml of suspension being preferred. The lyophilized powder form for the injectable may typically comprise from 0-0.2% by weight, or from about 0.09% to about 0.11% by weight buffering agent, if any.

2.7 Medicaments

The injectable implants may also contain a medicament. As used herein, a "medicament" may be any bioactive composition, pharmaceutical, drug or compound which one desires to administer to the site of the injection of the implant. For example, the medicament may comprise an anesthetic to decrease the pain or discomfort associated with injecting the implant or a composition that facilitates the integration of the polymer or decreases the trauma to the injection site. Exemplary anesthetics include but are not limited to lidocaine, xylocaine, novocaine, benzocaine, prilocaine, ripivacaine, and propofol.

Other medicaments that can be employed in the injectables disclosed herein include medicament comprises a peptide, a tissue regeneration agent, an antibiotic, a steroid, fibronectin, a cytokine, a growth factor, an analgesic, an antiseptic, alpha-, beta, or gamma-interferon, erythroietin, glucagons, calcitonin, heparin, interleukin-1, interleukin-2, filgrastim, cDNA, DNA, proteins, peptides, HGH, luteinizing hormone, atrial natriuretic factor, Factor VIII, Factor IX, and follicle-stimulating hormone. The medicament is often added to the injectable just prior to the injection during activation mixing with a pharmaceutically acceptable carrier.

3 Methods of Preparation of the Injectables

The injectables disclosed herein are typically made by combining particles containing a polymer containing lactic acid repeat units having the desired size and shape with glycolic acid and any other components, such as any cryoprotecting, buffering, gelling or tensoactive agents. The polymer may be obtained commercially or synthesized and/or modified by techniques and reactions that are well known by those of skill in the art. Polymeric particles having the desired shape and size are then preferably made by pulverizing the polymer to a powder; and cold micronizing the powder to the desired shape and size.

In preferred embodiments solutions containing the other components are obtained and then mixed with a slurry of the polymeric particles to form an emulsion, which is washed, filtered and ultimately dried to obtain a powder. This powder is then further processed (typically lyophilized) to form the pre-activated injectable implants. These pre-activated injectables are ultimately reconstituted, or activated, to form an activated suspension of polymeric particles.

An important step in preparing products based on microparticles or microspheres is the recovery of the solid from slurry and drying the final product. This becomes increasingly difficult as the size of the particles decreases. The standard methods such as centrifugation and filtration, followed by vacuum drying and lyophylization involve several transfer steps resulting in loss of product and risk of contamination, the latter being quite serious when an aseptic process is required, not withstanding 3 to 4 days required by the known standard methods.

The present method represents an advance over known methods as it is capable of separating microspheres from slurry media, washing them on the screen and drying the recovered microspheres. The original characteristics of the microspheres are maintained and the process time is no more than 7/8 hours.

4 Methods of Use of the Injectables

The injectables disclosed herein may be used as bulking agents to augment soft tissue in mammals in a variety of treatments, such as the cosmetic treatment of scars, wrinkles and facial fat loss, the treatment urinary or pyloric sphincter deficiency, such as deficiencies contributing to incontinence or acid reflux, the treatment of vocal cord paralysis, and the correction of congenital anomalies. The present injectables may also be used as drug delivery vehicles to administer a medicament to a mammal in need thereof. Preferred mammals for treatment are humans.

In these methods, the injectables are typically introduced into the tissue site to be treated or medicated typically by intradermal or subcutaneous syringe injection. Although any syringe may be employed, a carpules syringe is preferred.

4.1 Cosmetic Treatment of Scars, Wrinkles and Facial Fat Loss

The injectable implants of the present invention may be used to fill and smooth out soft tissue defects such as pock marks or scars (such as chicken pox or acne scars, congenital anomalies (such as cleft lips) and wrinkles. The implants may also be used as bulking agents to augment facial fat loss in the human.

The anatomical area for the efficient use of the injectable implant or injection site may be the skin typically of the facial region. Structurally, the skin consists of two principal parts: the epidermis 1, which is the outer, thinner portion, which is composed of epithelium and attached to the inner, thicker, connective tissue and a subcutaneous, adipose tissue (fat) 2. Typical injection sites for various cosmetic and lipodystrophy treatments are shown in FIG. 1 and include sites for treating acne scars and fine facial lines 3, deeper sites for treating wrinkles, creases and modeling of facial profile 4 and deeper sites 5 for treating lipodystrophy.

4.2 Treatment of Sphincter Deficiency (Urinary and Pyloric)

The injectables disclosed herein may be used to treat various sphincter deficiencies In instances of urinary incontinence, or after a prostatectomy in men, it is necessary to compress the urethra to assist the sphincter muscle to avoid leakage of urine from the bladder.

Urinary incontinence (loss of bladder control), has various classifications:

Stress due to physical movement (coughing, sneezing, exercising);

Urge or leakage of large amounts at unexpected times, including sleep; and

A mixture of these, that is, an occurrence of stress and urge together.

All types of incontinence can be treated regardless of the patient's age. Continence is dependent upon a compliant reservoir and sphincter efficiency that has 2 components: (1) the involuntary smooth muscle on the bladder neck 6; and (2) the voluntary skeletal muscle 7 of the external sphincter.

Figure 2A:
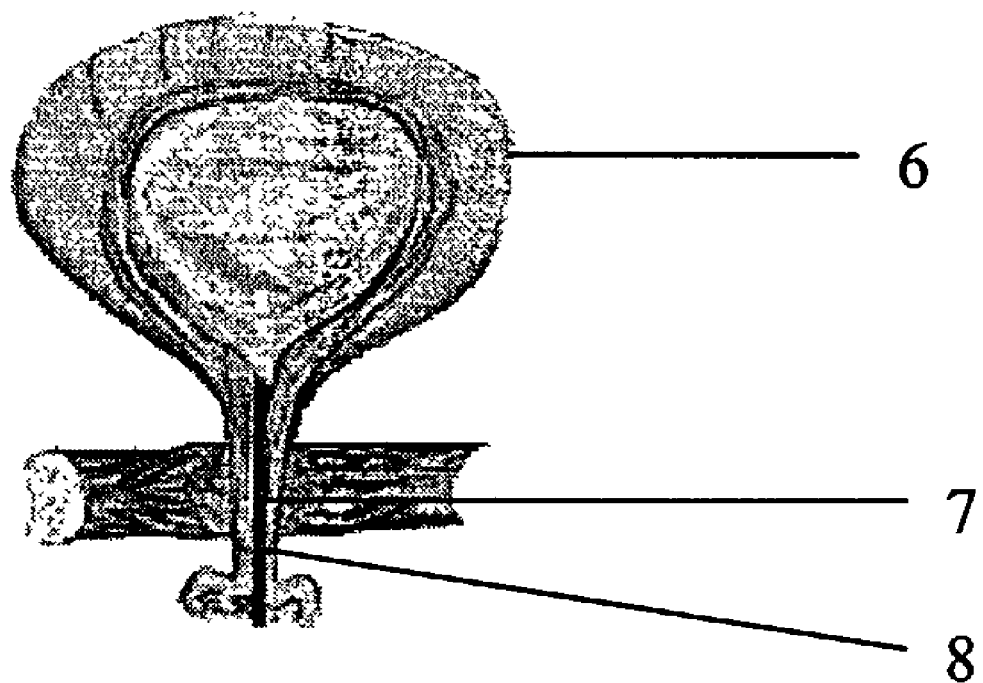
FIGS. 2A and 2B illustrates typical injection sites for the treatment of urethral sphincter deficiency.
Figure 2B:
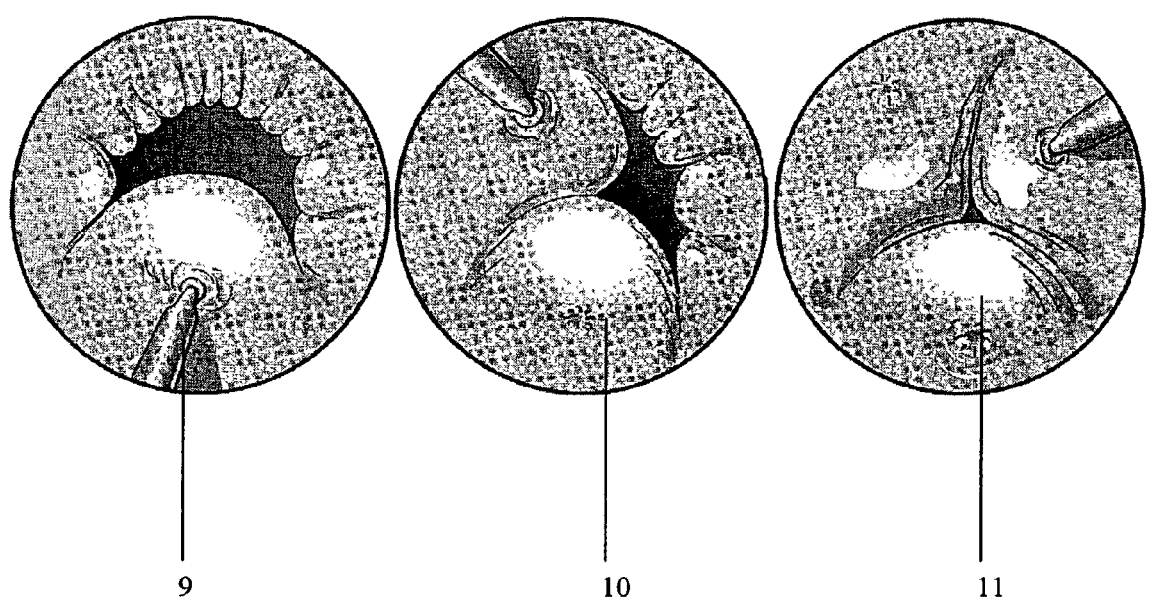

Thus, an aspect of the present invention encompasses using the disclosed bulking agents/injectables to add bulk and localize compression to the sphincter muscle or urethra 8, thereby reducing the lumen size through one or more injections of the bulking agent and thus substantially reduce or eliminate urinary stress incontinence, see FIGS. 2A and 2B. In these instances the implant may be inserted by injection into urethral or periurethral tissue. Thus, a typical procedure involves injecting the bulking agent with the aid of a cystoscope into the tissues around the neck of the bladder 6 creating increased tissue bulk, as shown in the photographic inserts 9-11 in FIG. 2B, and subsequent coaptation of the urethral lumen. The implant adds bulk and helps to close the urethra to reduce stress incontinence. The injection may typically be repeated yearly for optimal results. The product can be injected in about half an hour using local anesthesia.

In cases of acid reflux, the bulking agents may be used to treat a deficiency of the pyloric sphincter. Gastroesophageal reflux disease (GERD) involves the regurgitation of stomach 12 gastric acid and other contents into the esophagus 13 or diaphragm 14. 70% of reflux episodes occur during spontaneous relaxations of the lower esophageal sphincter, or due to a prolonged relaxation after swallowing. 30% occur during periods of low sphincter pressure. The primary symptom is heart burn (30 to 60 minutes after meals). Atypical manifestations of GERD include: asthma; chronic cough; laryngitis; sore throat; and non-cardiac related chest pain. GERD is a lifelong disease that requires lifestyle modifications as well as medical intervention.

Figure 3:
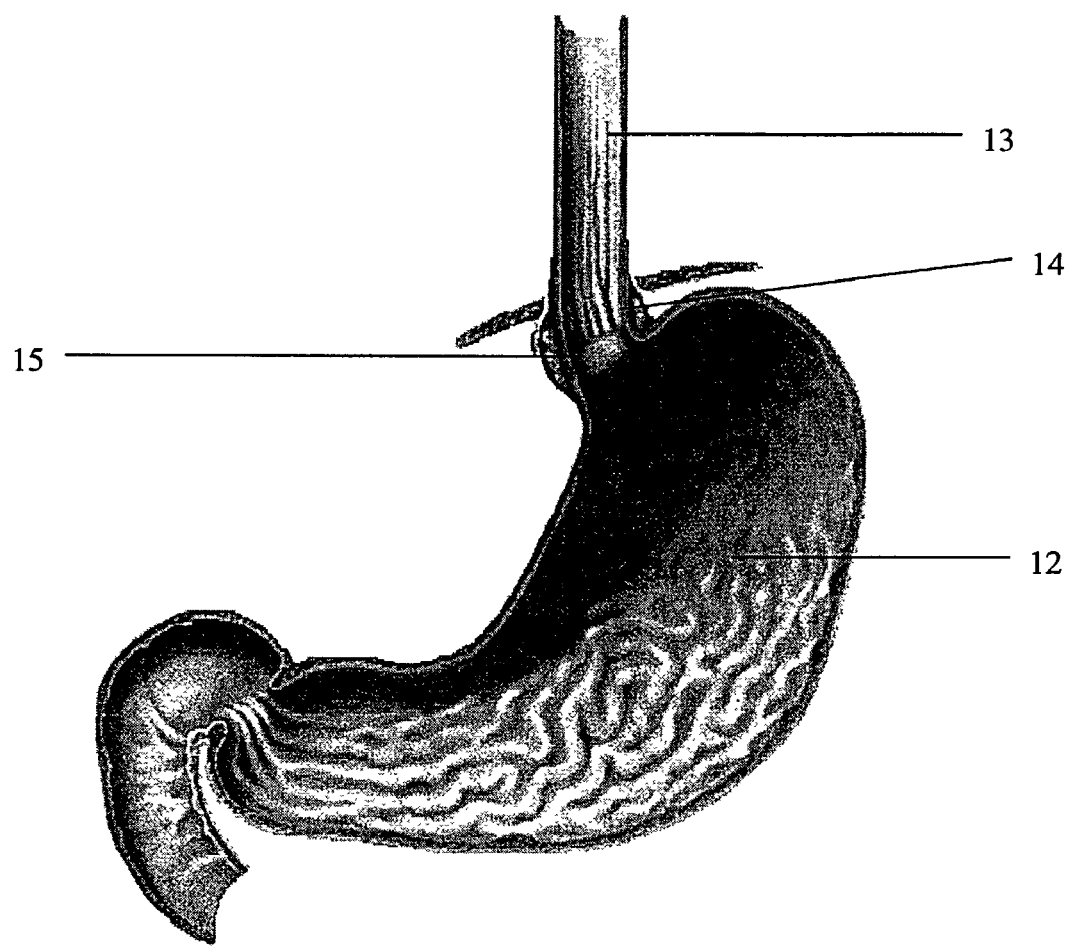
FIG. 3 illustrates typical injection site for the treatment of lower esophageal sphincter deficiency.

Thus, an aspect of the present invention encompasses using the disclosed bulking agents/injectables to add bulk and localize compression to the lower esophageal sphincter 15. Thus, a typical procedure involves injecting the bulking agent with the aid of a endoscope into the tissues around the lower esophageal sphincter 15 creating increased tissue bulk, see FIG. 3, and subsequent coaptation, normalizing sphincter pressure. The implant adds bulk and helps to close the sphincter to reduce reflux. The injection may be repeated yearly for optimal results. The product can be injected in about 45 minutes to one hour using local anesthesia.

4.3 Treatment of Erectile Dysfunction

Erectile dysfunction (ED), or the consistent inability to maintain an erection, is generally categorized as: organic, psychogenic, or both (organic and psychogenic). Most cases of male erectile disorders have an organic rather than a psychogenic cause. Organic ED is the result of an acute or chronic physiological condition, including endochrinologic, neurologic or vascular etiologies. Approximately 80% of cases are secondary to organic disease, 70% of those to arterial or venous abnormalities. Further, transient lost or inadequate erection affects men of all ages.

Figure 4:
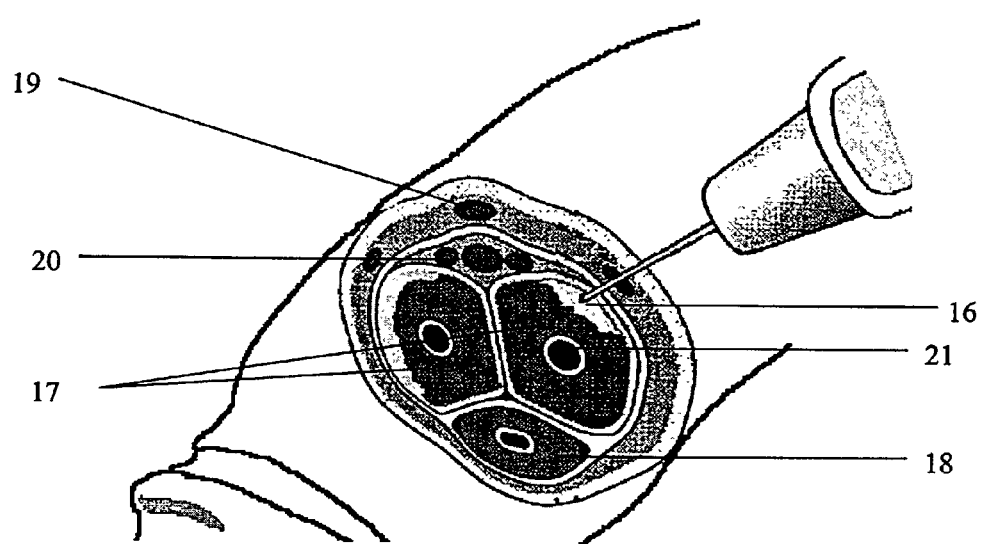
FIG. 4 illustrates typical injection site for the treatment of erectile dysfunction.

Thus, an aspect of the present invention encompasses using the disclosed bulking agents/injectables to treat ED. A typical procedure involves injecting the bulking agent directly at the deep fascia 16 throughout the length of the corpus cavernosum 17 as shown in FIG. 4 which also shows the urethra 18, the superficial dorsal vein 19, the deep dorsal vein 20, and the deep artery 21.

4.4 Treatment of Vocal Cords

An aspect of the present invention encompasses the use of the injectable implants disclosed herein as a bulking agent for intracordal injections of the laryngeal voice generator by changing the shape of this soft tissue mass.

4.5 Drug Delivery Vehicles

The present invention also relates to compositions and methods for providing controlled release of beneficial pharmaceutically active agents or medicaments.

As used herein "a" and "an" mean one or more.

The following examples are included to demonstrate preferred embodiments of the invention. It should be appreciated by those of skill in the art that the materials and techniques disclosed in the examples which follow represent materials techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Materials

The materials described below were employed in the Examples to exemplify certain preferred embodiments of the present invention. Other similar materials may also be employed.

Glycolic acid. Glypure®, a highly purified form of glycolic acid in which trace organic and inorganic impurities found in the technical grade have been minimized, was obtained from Du Pont Chemical Solutions Enterprise. Glypure® is a clear liquid solution containing 70% glycolic acid and 30% water in which the solution's total acid specification is 70%-72% and the typical free acid is 64.1%-66.7%. Glypure® exhibits a pH of 0.1 at 25° C. (77° F.) and a density of 1.25 g/cm³ at 26° C. (79° F.). In the examples, Glypure® is further diluted to 0.01%.

Polylactic acid. PURASORB® PL, a very pure poly 1-lactic acid ((3S-cis) 3,6-dimethyl-1,4-dioxane-2,5 dione homopolymer), was obtained from PURAC. PURASORB® PL is an odorless, water-insoluble white crystalline solid having a density of 1.24 kg/l; an intrinsic viscosity range of from 3.5-4.5 dl/g in chloroform at 25° C., target 3.62 dl/g; a molecular weight range determined by viscosity of from 170,000 to 220,000 Dalton, target 172,000; a specific optical rotation (in chloroform at 20° C.) of about −156.6°, a melting point range of from about 170-200° C. (determined by differential scanning calorimetry ("DSC"), 10° C./min), target from 178.0-190.1° C.; and a heat of fusion (determined by DSC, 10° C./min) of about 86.5 J/g.

PURASORB® PL contains <0.01% residual solvent (toluene and ethyl acetate) as determined by head space gas chromatography and <0.1% monomer as determined by GC. Water content was determined by the Karl Fisher method.

Hydroxypropylmethylcellulose. Hydroxypropylmethylcellulose ("HPMC"), a methylcellulose propyleneglycol ether, is commercially available from numerous vendors. The HPMC so obtained was typically dried for about 2 hours at 105° C.

D-Mannitol. D-mannitol, a crystalline white dust, is commercially available from numerous vendors. The d-mannitol employed in the Examples contained no less than 96.0% and no more than 102.0% of $C_6H_{14}O_6$ calculated against the dry chemical. D-mannitol is readily soluble in water, soluble in alkaline solutions, slightly soluble in pyridine, very soluble in ethanol, and virtually insoluble in ether.

Di-Basic Sodium Phosphate. Di-basic sodium phosphate may be anhydrous or in hydrated form (e.g., $Na_2HPO_4.7H_2O$) and is a white or colorless granular salt. The $Na_2HPO_4$ employed in the Examples contained no less than 98% and no more than 100.5% of di-basic sodium phosphate, calculated with the reference of a dry chemical and was readily soluble in water and only very slightly soluble in ethanol.

EXAMPLE 2

Preparation of Injectables

The following general procedure was used to prepare the injectables described in the examples.

Phase I: Preparation of Mixtures

PLA (1 kg) was weighed and subjected to a two-step grinding process. First, the PLA (coarse polymer crystals for 1-PLA) was pulverized to a powder of: ±150/200μ with a verified loss of ±5%, resulting in approximately 950 g. usable processed polymer. This powder was then cold micronized (at −80° C.) under an atmosphere of $N_2$ to obtain a powder of microspheres with diameters ranging from about 40μ to about 80μ and a mean diameter of about 60μ, by pressure of gasified $N_2$ filtered in at a ratio of 0.20μ observing a temperature (critical) of −80° C., SCFM air @ 70° F. & 100 PSIG, steam (lb/hr) @ 700° F. & 200 PSIG, with a verified loss of ±10%, resulting in approximately 855 g. of usable processed polymer.

The spheres were then prepared with a high-emulsion technique to obtain the hydrophobic PLA spheres. The grinded PLA (±855 g) was dissolved in a stainless steel vessel (mirror finish interior) in 10 l of $CH_2CL_2$ (chloroform). To this mixture was added 2.6 ml of 1.7 M NaCl and 2% of PVA (polyvinyl alcohol) per 10 g of PLA (10% wt/wt to chloroform/sodium). This was emulsified by vortexing vigorously for five minutes to obtain the hydrophobic spheres. The mixture produced in the vortex was then subjected to an acoustic-room sonic system for 10 minutes.

35 ml of glycolic acid was diluted (0.1 ml) to 0.01% in 350 ml of bio-distilled de-mineralized water.

HPMC (414.750 g) and d-mannitol (595 g) were added to 2 l chloroform and 5 l of water (ppi) under $N_2$ atmosphere, mixed and vigorously emulsified in a vortex, typically for about 15 minutes depending upon volume, altitude and temperatures.

The tensoactive agent (polyoxoethylene sorbitan monooleate (Tween 80) (22.5 g)) and PH stabilizers (buffering agents—sodium phosphate dibasic (0.583 g), sodium phosphate monobasic (1.166 g)) were combined under $N_2$ atmosphere with 5 l water ppi and mixed vigorously for thirty minutes.

Phase II: Integral Mixing

The above four solutions were poured into a pressure heating tank and heat (under $N_2$ atmosphere) at 80° C. to evaporate the solvents. Vigorous mixing (700 rpm) was sustained for 3 hours throughout the heating process. (About 95% of the water is evaporated and the residue is a sludge which is further freeze-dried during a later step to remove substantially all of the water).

Phase III: Solid Product Isolation

A PharmaSep® operational unit was used for aseptic transference of all solids contained in the final mixture and removal of the fluid means from the mixture, as well as for the drying of the solid product collected via purged-air/vacuum application for recovery of dry particles. The unit also facilitated particle washing and rinsing before drying. Upon completion of rinsing, all captured microspheres were dried by simultaneous application of vacuum and introduction of dry air. Dried microspheres were downloaded through a download plug.

Specifically, the microsphere residue/aqueous slurry from Phase II was introduced through the input or feeding port at a predetermined optimum rate (typically about 200 grams per minute) while the unit was vibrating. In order to obtain optimal movement in the product's sieve, the regulator of the unit was adjusted to the maximum weight point of 100% and the minimum weight point of 90% with the main control angle at 30 degrees; with these parameters the unit obtains a 0.052-inch horizontal amplitude, a 0.104-inch vertical amplitude, and a 34.7 degree phase angle at the product's sieve.

An upper screen was used, which had a 150μ sieve mesh of material and a 6 inch screen for the product which was a 25μ sieve mesh of material. The motor's speed was fixed at 1,800 rpm. Vibration was maintained throughout all of the drying stage.

Microsphere solids were introduced in the unit through the feedhole at an optimal predetermined pace while the machine was vibrating. Add-ons and larger microspheres were collected at the upper mesh and the microspheres with the size range 40μ to 80μ were collected in the mesh of the product. The extrafine microspheres, with size less than 40μ were expelled along with the means through the drain conduit. Microspheres collected at the product's mesh were rinsed 5 times with 300 ml of double distilled water. After rinsing, the collected microspheres were dried by application of vacuum (22 inches mercury) at the upper part, and below the mesh, under a nitrogen atmosphere (100-299 mL/min) measured by a flowmeter.

The drying period was 7-8 hours at room temperature. Dried, purged air (nitrogen) was introduced to facilitate expulsion of humidity and residual solvent. The extrafine microspheres passing through the product's mesh, during introduction of solids and the drying period, were collected by a filtration membrane (pore size 0.45μ), vacuum-dried and categorized. Loss was verified at between 6-8%.

Process Control. In order to verify the effect of the drying process on the microspheres, approximately 1.6 liters of solids were divided in 3 identical fractions (3 secondary batches).

Microsphere Analysis: Each secondary batch of microspheres was evaluated to establish performance, humidity content, particle size, surface morphology, mass density and specific surface area.

The humidity content was calculated using a humidity analyzer.

The distribution of the average microsphere size was calculated using a laser gauge.

The specific surface was calculated using a BET Analyzer.

The surface morphology was checked by Scanning Electron Microscope.

Phase IV: Bottling, Freeze Drying and Final Product Preparation

Vials (7 mm glass/22 diameter) were filled with 475.74 mg of the dried powder from the Vibro Filter Dryer® and closed with special rubber tops for injectable products (bromobuthyl). The powder was then freeze dried for 36 hours at −28° C., vacuum pressure of 50 microbares, euteutic set of 10° C. A white uniform dry pellet resulted, covering approximately the bottom third of the vial. Approved lot vials containing the dried lyophilized injectables were sealed with plastic (PVC) and aluminum security ring, and then sterilized with gamma rays (λ)

EXAMPLE 3

Exemplary Formulations

A lyophilized jar contained:

| COMPONENTS | Mass (mg) | % |
|---|---|---|
| Glycolic Acid (GA) | 0.07 | 0.01 |
| Polylactic Acid (PLA) | 200.00 | 40.81 |

-continued

| COMPONENTS | Mass (mg) | % |
|---|---|---|
| Hydroxypropylmethylcellulose (HPMC) | 118.33 | 24.14 |
| D-Manitol apirogen | 170.00 | 34.69 |
| pH Stabilizer (di-basic sodium phosphate buffer) | 0.50 | 0.10 |
| Surfactant (Tween 80) | 1.20 | 00.24 |
| Total | 490.10 | 99.99 |

This was activated extemporaneously with 5.5 ml of double distilled water for injectable preparations to produce the following injectable:

| COMPONENTS | Mass (mg) | % |
|---|---|---|
| Glycolic Acid (GA) | 0.07 | 0.0012 |
| Polylactic Acid (PLA) | 200.00 | 3.34 |
| Hydroxypropylmethylcellulose (HPMC) | 118.33 | 1.98 |
| D-Manitol apirogen | 170.00 | 2.84 |
| pH Stabilizer (di-basic sodium phosphate buffer) | 0.50 | 0.0083 |
| Surfactant (Tween 80) | 1.20 | 0.02 |
| Double distilled water | 5,500 | 91.82 |
| Total | 5,990.10 | 100.00 |

EXAMPLE 4

Animal and Clinical Studies

The injectable implants and bulking agents were used in animal studies and clinical trials to determine their efficacy and safety.

The following general procedure was used for clinical studies evaluating lipodystrophy and cosmetic procedures employing the injectable bulking agents and implants disclosed herein. Prior to application, a thorough aseptic cleaning of the area to be treated is done with surgical soap and iodine and the area to be treated is marked. 3 ml syringes (e.g., insulin-type) with 26 gauge needles are employed (with the needles destroyed after use). Depending upon the type of treatment, a local or regional anesthetic may be applied. For example, local anesthesia or blocking of branch nerve (infiltrated per cutaneous or oral mucosa) with lidocaine 2% in water may be used for pain relief. The injectable implant is injected with the needle at an angle of between 45° to 55° in designed facial quadrants. A reflux is done to corroborate that no blood vessel has been punctured. The facial quadrants are infiltrated by using "tunneling" (that is, at the same time the product is being injected the needle is slowly being subtracted, creating a tunnel where the product remains) and "grill" (that is, tunneling in crisscross fashion) techniques. A tactual over-correction of about 10% to 20% is to be carried out with gentle massage of the area to diffuse the product regularly. Immediately after the injection, an ice pack is applied for 5 to 10 minutes to avoid ecchymosis and/or an edema of the infected area.

Clinical Trials in Animals:

An animal study was carried out between October 2000 and February 2001. The animals used were laboratory mice (48), divided in 6 groups of 8 mice each. Each 8 mice on the 6 groups were injected in 4 different body areas with a dose of 0.2 cc of the constituted formula of glycolic and polylactic acids of Example 3. Subsequently, each group was divided into 4 subgroups with 2 mice in each group.

Controls were carried 3 days after the start of the program, and 15, 45 and 90 days afterwards. At each control period, 8 biopsies were done in each tissue. The object was to detect reactions such as inflammation, fibrosis, encapsulation, and absorption.

The designated body parts to be treated were the dermis; mucosa; perichondric and cartilage (sub-perichondric administration and biopsy of both); sub-cutaneous cellular tissue; muscle; periosteum and bone (sub-periosteum administration and studies of both).

All mice were marked and labeled according to international standards (GCP).

The tissue response to the absorption of the product at the dermis, subcutaneous cellular tissue, mucosa, and muscle was minimal during the first days, as the foreign body material was found in extra cellular form.

In a longer length of time the absorption gradually incremented, determined by the intracellular for of the foreign body.

As to the reaction at the perichondric and cartilage, the positive data of phagocytosis were found in the perichondric and soft adjacent tissues. Cartilage was intact in all cuts and no absorption was reported in any of the cartilage cells.

At the periosteum and bone, it was observed that the foreign body (PLA), took longer time to present itself in intracellular form at the periosteum and soft tissues. No material was found at the bone spicule.

As a result of these tissue responses, it was concluded that the formulation of GA and PLA is a bioabsorbable combination. The absorption takes place slowly since extracellular foreign material was found at the end of the 90 day period. The absorption rate was determined by the appearance of the product in intracellular form. A higher concentration of the product was found over the long term, mainly in soft tissues (dermis, subcutaneous cellular tissue, mucosa and muscle). At the perichondrium and periosteum, absorption took place in a lesser degree. There was no absorption in the cartilage or bone.

The formula first conditions an acute inflammatory response, and in the long term, it manifests itself as a chronic and granulomatosis reaction on a larger scale.

Results on Trials with Glycolic Acid in Guinea Pigs:

In a preliminary test, 39 guinea pigs were used to define product concentration for intradermal injections. All were adult animals and sex was not considered. They were divided in 4 different cages, each containing 9, 10, 10 and 10 animals. The glycolic acid was dissolved in a propyl glycolic aqueous solution qsp. Evaluations were taken after the $3^{rd}$ and $7^{th}$ day.

At a dosage of 0.1 ml at 0.1%, there was tissue necrosis on the 3 day and ulcer on the $7^{th}$ day.

At a dosage of 0.1 ml at 0.3% the was evident hyperaemia edema on the $3^{rd}$ day, and epydermolyse and edema on the $7^{th}$ day.

At a dosage of 0.1 ml at 0.2% there was a moderate hyperaemia and edema on the $3^{rd}$ day, and normal tissue (regular) on the $7^{th}$ day.

At a dosage of 0.1 ml at 0.01%, 40% of the animals showed a minimal oedema and hyperaemia with no edema and no hyperaemia in the remainder 60% animals.

By the results of the trials, it was concluded that the acceptable glycolic acid dosage varied between 0.02% to 0.01%, being the latter the ideal dose.

Results on Trials with Glycolic Acid in Humans:

A group of 35 human patients received an intradermal application of 5 ml of glycolic acid at 0.01% and no adverse reactions was reported in tissues of bearing hyperemia, edema or discreet ecchymosis. In comparison to the retinoids, which have a more intense action as per the collagen synthesis and the immune regulator effects in the tissues, the glycolic acid presents low local toxicity, no systemic effect or comedomic action. (Personelli)

Results on Treatment of Facial Lipodystrophy in Humans:

Clinical trials in humans were also conducted to establish that the injectable implants disclosed herein are innocuous, safe, bio-absorbable, and easily assimilated by the receptor (eg., patients with facial lipodystrophy) with satisfactory and lasting results.

Dosage: Each patient received a dose equivalent to 1 or 2 vials. Each vial contained 490.1 mg of freeze dried product constituted with 5.5 ml of injectable (demineralized and distilled) water for a total per vial of 5,990.1 mg. The areas and dosage applied were the following:

| Lipo-dystrophy | Affected area | $ of fat loss | N° of sessions | Dose per side | Injected area |
| --- | --- | --- | --- | --- | --- |
| Mild 5 patients | Malar | 10-20% | 2 | 3-4 cc | Superficial intradermal |
| Moderate 12 patients | Malar, deep smile lines, Bichat area | 20-30% | 3 | 4-5 cc | Superficial and deep intradermal |
| Severe 10 patients | Bichat area, deep smile lines, inner mandibula, frontal temporal, malar temporal | 30-50% | 4 | 5-8 cc | Superficial and deep intradermal & subcutaneous |
| Extreme 5 patients | Bichat area, deep smile lines, inner mandibula, front temporal, malar temporal, zygomatic | 50% | 5 | 6-10 cc | Superficial and deep intradermal & subcutaneous |

Support: Patient's full clinical history, height, weight, age, photo study front & sides (before and after treatment-sessions), Doppler and biopsies.

All procedures in compliance with GCP, Helsinki Convention.

Results

After the first session, 26 patients presented a mile edema which lasted less than 12 hours, mainly due to the effect of the anesthetic (Lidocaine) as well as a response to the presence of the foreign body and the mechanical aggression to the tissues by the needle. Only 1 patient presented a mild unilateral ecchymosis.

After the second session, 11 patients presented an idiopathic or artificial edema with no adverse reactions, allergies or any other type of complications.

After the third session an idiopathic edema was present in 8 patients, 1 patient had a moderate edema which was absorbed in 48 hours, and 1 patient presented a mild ecchymosis.

| Period after last session | Correction of facial contour | Adverse reactions | Absorption % |
| --- | --- | --- | --- |
| 30 days | 75% | 0 | 0 |
| 90 days | 85% | 0 | 2% |

-continued

| Period after last session | Correction of facial contour | Adverse reactions | Absorption % |
|---|---|---|---|
| 120 days | 100% | 0 | 3% |
| 180 days | 80% | 0 | 10% |

As an example, volume recuperation showed the following results in one patient:

| Date previous | Area | Left malar area (cheek) | Right malar area (cheek) |
|---|---|---|---|
| 1st treatment May 14, 2001 | Epidermis | 0.07 cm | 0.05 cm |
| | Dermis | 0.29 cm | 0.22 cm |
| Date after 3rd Jul. 02, 2001 | Epidermis | 0.08 cm (+0.01 cm) | 0.07 cm (+0.02 cm) |
| | Dermis | 0.33 cm (+0.04 cm) | 0.30 cm (+0.08 cm) |

While the present invention has been described in terms of specific embodiments, it is understood that variations and modifications will occur to those skilled in the art. Accordingly, only such limitations as appear in the claims should be placed on the invention.

What is claimed is:

1. A biodegradable, injectable implant comprising glycolic acid monomer and particles comprised of a polymer comprising lactic acid repeats units, wherein the particles have a diameter of from about 20 μ to about 120 μ and are suspended in a pharmaceutically accentable carrier, and the glycolic acid monomer is present in a concentration of from about 1.8 mcg to about 18.2 mcg glycolic acid monomer per 100 ml of the pharmaceutically acceptable carrier.

2. The implant of claim 1, wherein the particles have a diameter of from about 40μ to about 80μ.

3. The implant of claim 2, wherein the particles have a mean diameter of from about 50μ to about 70μ.

4. The implant of claim 1, wherein the pharmaceutically acceptable carrier comprises water, saline, starch, hydrogel, polyvinylpyrrolidone, polysaccharide, hyaluronic acid ester, or plasma.

5. The implant of claim 1, wherein the polymer is present in a concentration of from about 30 mg to about 40 mg of polymer per 100 ml of the pharmaceutically acceptable carrier.

6. The implant of claim 5, wherein the polymer is present in a concentration of from about 35 mg to about 38 mg per 100 ml of the pharmaceutically acceptable carrier.

7. The implant of claim 1, wherein the glycolic acid monomer is present in a concentration of from about 11 mcg to 14 mcg per 100 ml of the pharmaceutically acceptable carrier.

8. The implant of claim 1 further comprising a gelling agent.

9. The implant of claim 8, wherein the gelling agent comprises a cellulose derivative or a pharmaceutically acceptable acid or ester.

10. The implant of claim 9, wherein the cellulose derivative comprises hydroxypropylmethylcellulose or carboxymethylcellulose.

11. The implant of claim 9, wherein the pharmaceutically acceptable acid or ester is selected from the group consisting of a synthetic hyaluronic acid, a lactic acid ester, sodium carmellose, and a caproic acid ester.

12. The implant of claim 1 further comprising a surfactant.

13. The implant of claim 12, wherein the surfactant comprises a polyoxyethylene sorbitan, a polysorbate or pluronic acid.

14. The implant of claim 13, wherein the polyoxyethylene sorbitan comprises polyoxyethylene sorbitan monooleate, polyoxyethylene sorbitan trioleate, polyoxyethylene sorbitan monostearate, polyoxyethylene sorbitan tristearate, polyoxyethylene sarbitan monopalmitate, or polyoxyethylene sorbitan monolaurate.

15. The implant of claim 1, wherein the polymer comprises a homopolymer of lactic acid.

16. The implant of claim 15, wherein the polymer comprises poly-1-lactic acid or poly-d,1-lactic acid.

17. The implant of claim 1, wherein the polymer comprises a co-polymer of lactic acid.

18. The implant of claim 17, wherein the polymer comprises a co-polymer of lactic acid and glycolic acid.

19. The implant of claim 17, wherein the polymer comprises repeat units capable of forming crosslinks.

20. The implant of claim 17, wherein the polymer comprises at least one lactone repeat unit.

21. The implant of claim 1, wherein the polymer has an intrinsic viscosity of from about 3.5 to about 3.8 dl/g.

22. The implant of claim 1, wherein the polymer has a molecular weight of from about 150,000 to about 220,000 Daltons.

23. The implant of claim 22, wherein the polymer has a molecular weight of from about 165,000 to 180,000 Daltons.

24. The implant of claim 23, wherein the polymer has a melting point ranging from about 170 to about 200° C.

25. The implant of claim 1 further comprising a cryoprotecting agent.

26. The implant of claim 25, wherein the cryoprotecting agent comprises d-mannitol, lactose, sucrose, fructose, a sugar, a carbohydrate, or dextran.

27. The implant of claim 1 further comprising a buffering agent.

28. The implant of claim 27, wherein the buffering agent comprises a phosphate buffer or a citrate buffer.

29. The implant of claim 1, wherein the implant is ma vial in the form of a sterile suspension.

30. The implant of claim 1, wherein the implant further comprises particles comprised of a polymer comprising lactic acid repeats units and wherein the implant is formed by the suspension of a lyophilized powder of the particles in the pharmaceutically acceptable carrier.

31. The implant of claim 30, wherein from about 0.002% to about 0.02% by weight of the implant is glycolic acid monomer.

32. The implant of claim 31, wherein from about 0.01% to about 0.02% by weight of the implant is glycolic acid monomer.

33. The implant of claim 30, wherein the lyophilized powder comprises from about 36% to about 45% polymer by weight.

34. The implant of claim 33, wherein the lyophilized powder comprises from about 40% to about 41% polymer by weight.

35. The implant of claim 1, wherein the implant has been sterilized by gamma or E-beam irradiation or exposure to ethylene oxide gas.

36. The implant of claim 1, further comprising a medicament.

37. The implant of claim 36, wherein the medicament comprises a peptide, a tissue regeneration agent, an anesthetic, an antibiotic, a steroid, fibronectin, a cytokine, a growth factor, an analgesic, an antiseptic, alpha-, beta- or gamma-interferon, erythroietin, glucagons, calcitonin, heparin, interleukin-1, interleukin-2, filgrastim, cDNA, DNA, PROTEINS, PEPTIDES, HGH, luteinizing hormone, atrial natriuretic factor, Factor VIII, Factor IX, or follicle-stimulating hormone.

38. The implant of claim 37, wherein the medicament comprises an anesthetic which is selected from the group consisting of lidocaine, xylocaine, novocaine, benzocaine, prilocaine, ripivacaine, and propofol.

39. A biodegradable, injectable implant comprising glycolic acid monomer and particles comprised of polylactic acid, wherein the particles have a mean diameter of from about 40μ to about 80μ and are suspended in a pharmaceutically acceptable carrier, and the glycolic acid monomer is present in a concentration of from about 1.8 mcg to about 18.2 mcg glycolic acid monomer per 100 ml of the pharmaceutically acceptable carrier.

40. The implant of claim 39, wherein the particles have a mean diameter of from about 55μ, to about 65μ.

41. The implant of claim 39, wherein the polylactic acid comprises poly-1-lactic acid or poly-d,1-lactic acid, or co-polylactide-polyglycolide.

42. The implant of claim 39, wherein the polylactic acid has an intrinsic viscosity of from about 3.6 dl/g to about 3.8 dl/g.

43. The implant of claim 39, wherein the polylactic acid has a molecular weight as determined by viscosity from about 150,000 to about 180,000 Daltons.

44. The implant of claim 39, wherein the pharmaceutically acceptable carrier comprises water.

45. The implant of claim 44, wherein the pharmaceutically acceptable carrier comprises saline, starch, hydrogel, polyvinylpyrrolidone, polysaccharide, hyaluronic acid ester, or plasma.

46. The implant of claim 44, wherein the polylactic acid is present in a concentration of from about 30 mg to about 40 mg of polymer per 100 ml of the pharmaceutically acceptable carrier.

47. The implant of claim 39 further comprising a gelling agent.

48. The implant of claim 47, wherein the gelling agent comprises a cellulose derivative or a pharmaceutically acceptable acid or ester.

49. The implant of claim 48, wherein the cellulose derivative comprises hydroxypropylmethylcellulose or carboxymethylcellulose.

50. The implant of claim 48, wherein the pharmaceutically acceptable acid or ester comprises a synthetic hyaluronic acid, a lactic acid ester, sodium carmellose, or a caproic acid ester.

51. The implant of claim 39 further comprising a surfactant.

52. The implant of claim 51, wherein the surfactant comprises a polyoxyethylene sorbitan, a polysorbate or pluronic acid.

53. The implant of claim 52, wherein the polyoxyethylene sorbitan comprises polyoxyethylene sorbitan monooleate, polyoxyethylene sorbitan trioleate, polyoxyethylene sorbitan monostearate, polyoxyethylene sorbitan tristearate, polyoxyethylene sorbitan monopalmitate, or polyoxyethylene sorbitan monolaurate.

54. The implant of claim 39 further comprising a cryoprotecting agent.

55. The implant of claim 54, wherein the cryoprotecting agent comprises d-mannitol, lactose, sucrose, fructose, or dextran.

56. The implant of claim 39 further comprising a buffering agent.

57. The implant of claim 56, wherein the buffering agent comprises a sodium phosphate or a citrate buffer.

58. The implant of claim 39, wherein the implant is in a vial in the form of a sterile suspension.

59. The implant of claim 39, wherein the implant comprises particles comprised of a polymer comprising lactic acid repeats units and wherein the implant is formed by the suspension of a lyophilized powder of the particles in a pharmaceutically acceptable carrier.

60. The implant of claim 59, wherein from about 0.002% to about 0.02% by weight of the implant is glycolic acid monomer.

61. The implant of claim 60, wherein the lyophilized powder comprises from about 36% to about 45% polymer by weight.

62. The implant of claim 39 further comprising a medicament selected from the group consisting of an anesthetic, a peptide, a tissue regeneration agent, an antibiotic, a steroid, fibronectin, a cytokine, a growth factor, an analgesic, an antiseptic, alpha-, beta, or gamma-interferon, erythroietin, glucagons, calcitonin, heparin, interleukin-1, interleukin-2, filgrastim, cDNA, DNA, PROTEINS, PEPTIDES, HGH, luteinizing hormone, atrial natriuretic factor, Factor VIII, Factor IX, and follicle-stimulating hormone.

63. A biodegradable, injectable implant comprising: a) glycolic acid monomer, wherein the glycolic acid monomer is present in a concentration of from about 12 mcg to about 13 mcg glycolic acid monomer per 100 ml of suspension; b) particles of polylactic acid, wherein the particles have a mean diameter of from about 40μ to about 80μ; c) a gelling agent; d) a surfactant; e) a cryoprotecting agent; and f) a buffering agent, wherein the implant comprises an aqueous suspension of particles of the polylacticacid.

64. The implant of claim 63, wherein the polylactic acid is poly-1-lactic acid or poly-1,d-lactic acid.

65. The implant of claim 63, wherein the polylactic acid has a molecular weight of from about 160,000 to about 180,000 Daltons.

66. The implant of claim 63, wherein the polylactic acid is present in a concentration of from about 30 mg to about 40 mg of polymer per 100 ml of suspension.

67. The implant of claim 63, wherein the gelling agent comprises hydroxypropylmethylcellulose or carboxymethylcellulose.

68. The implant of claim 63, wherein the surfactant comprises a polyoxyethylene sorbitan.

69. The implant of claim 63, wherein the cryoprotecting agent comprises d-mannitol.

* * * * *